United States Patent
Yu et al.

(10) Patent No.: US 11,135,153 B2
(45) Date of Patent: Oct. 5, 2021

(54) HIGH PENETRATION COMPOSITION AND USES THEREOF

(71) Applicant: Techfields Pharma Co., Ltd., Suzhou, Jiangsu (CN)

(72) Inventors: Chongxi Yu, Kensington, MD (US); Lina Xu, Shanghai (CN)

(73) Assignee: TECHFIELDS PHARMA CO., LTD., Jiangsu (CN)

( * ) Notice: Subject to any disclaimer, the term of this patent is extended or adjusted under 35 U.S.C. 154(b) by 0 days.

(21) Appl. No.: 15/379,866

(22) Filed: Dec. 15, 2016

(65) Prior Publication Data

US 2017/0151337 A1 Jun. 1, 2017

Related U.S. Application Data

(60) Division of application No. 12/397,308, filed on Mar. 3, 2009, now abandoned, which is a continuation-in-part of application No. 12/351,804, filed on Jan. 9, 2009, now abandoned, and a continuation-in-part of application No. PCT/IB2006/053091, filed on Sep. 3, 2006, said application No. 12/351,804 is a continuation-in-part of application No. PCT/IB2006/053741, filed on Oct. 11, 2006, and a continuation-in-part of application No. PCT/IB2006/053090, filed on Sep. 3, 2006, and a continuation-in-part of application No. PCT/IB2006/052815, filed on Aug. 15, 2006, and a continuation-in-part of application No. PCT/IB2006/052732, filed on Aug. 8, 2006, and a continuation-in-part of application No. PCT/IB2006/052575, filed on Jul. 27, 2006, and a continuation-in-part of application No. PCT/IB2006/052563, filed on Jul. 26, 2006, and a continuation-in-part of application No. PCT/IB2006/052549, filed on Jul. 25, 2006, and a continuation-in-part of application No. PCT/IB2006/052461, filed on Jul. 18, 2006, and a continuation-in-part of application No. PCT/IB2006/052318, filed on Jul. 9, 2006.

(Continued)

(51) Int. Cl.
| | |
|---|---|
| *A61K 31/167* | (2006.01) |
| *A61K 31/22* | (2006.01) |
| *A61K 31/612* | (2006.01) |
| *A61K 47/54* | (2017.01) |
| *C07C 231/12* | (2006.01) |
| *C07C 233/25* | (2006.01) |
| *A61K 9/00* | (2006.01) |
| *A61K 9/70* | (2006.01) |

(52) U.S. Cl.
CPC .......... *A61K 9/0014* (2013.01); *A61K 9/7023* (2013.01); *A61K 31/167* (2013.01); *A61K 31/22* (2013.01); *A61K 31/612* (2013.01); *A61K 47/54* (2017.08); *A61K 47/542* (2017.08); *C07C 231/12* (2013.01); *C07C 233/25* (2013.01)

(58) Field of Classification Search
CPC .... A61K 31/167; A61K 31/22; A61K 31/612; A61K 47/54; A61K 47/542; A61K 9/0014; A61K 9/7023; C07C 231/12; C07C 233/25
See application file for complete search history.

(56) References Cited

U.S. PATENT DOCUMENTS

| | | | |
|---|---|---|---|
| 1,815,802 | A | 7/1931 | Schleicher et al. |
| 2,671,805 | A | 3/1954 | Krimmel et al. |

(Continued)

FOREIGN PATENT DOCUMENTS

| | | |
|---|---|---|
| AU | 2004201178 A1 | 4/2004 |
| CA | 1246446 | 12/1988 |

(Continued)

OTHER PUBLICATIONS

Gould, P.L., "Salt selection for basic drugs" International Journal of Pharmaceutics, 1986, vol. 33, pp. 201-217.*

(Continued)

*Primary Examiner* — Yong S. Chong
(74) *Attorney, Agent, or Firm* — Fox Rothschild LLP

(57) ABSTRACT

The present invention relates to compositions and uses of novel high penetration compositions or high penetration prodrugs (HPP), in particular HPPs for 4-aminophenol derivatives, which are capable of crossing biological barriers with high penetration efficiency. The HPPs herein are capable of being converted to parent active drugs or drug metabolites after crossing the biological barrier and thus can render treatments for the conditions that the parent drugs or metabolites can. Additionally, due to the ability of penetrating biological barriers, the HPPs herein are capable of reaching areas that parent drugs may not be able to access or to render a sufficient concentration at the target areas and therefore render novel treatments. The HPPs herein can be administered to a subject through various administration routes. For example, the HPPs can be locally delivered to an action site of a condition with a high concentration due to their ability of penetrating biological barriers and thus obviate the need for a systematic administration. For another example, the HPPs herein can be systematically administer to a biological subject and enter the general circulation with a faster rate.

12 Claims, 3 Drawing Sheets

Related U.S. Application Data

(60) Provisional application No. 61/120,052, filed on Dec. 4, 2008.

(56) References Cited

U.S. PATENT DOCUMENTS

| | | | |
|---|---|---|---|
| 3,365,483 A | 1/1968 | Jerzmanowska et al. | |
| 3,420,871 A | 1/1969 | Scherrer et al. | |
| 3,476,791 A | 11/1969 | Newman et al. | |
| 3,488,380 A | 1/1970 | Goldhamer et al. | |
| 3,704,298 A | 11/1972 | Zinnes et al. | |
| 3,787,324 A | 1/1974 | Zinnes et al. | |
| 3,814,811 A | 6/1974 | Batllo et al. | |
| 3,821,279 A | 6/1974 | Kurono et al. | |
| 3,822,258 A | 7/1974 | Zinnes et al. | |
| 3,956,363 A | 5/1976 | Shen et al. | |
| 3,957,764 A | 5/1976 | Lund | |
| 3,966,923 A | 6/1976 | Serre | |
| 4,006,181 A | 2/1977 | Cousse et al. | |
| 4,012,508 A | 3/1977 | Burton | |
| 4,035,376 A | 7/1977 | Janssen et al. | |
| 4,044,049 A | 8/1977 | Ruyle et al. | |
| 4,127,671 A | 11/1978 | Cognacq | |
| 4,146,637 A | 3/1979 | Metz et al. | |
| 4,180,662 A | 12/1979 | Pfister et al. | |
| 4,180,665 A | 12/1979 | Schwander et al. | |
| 4,206,220 A | 6/1980 | Sloan | |
| 4,207,332 A | 6/1980 | Hayashi et al. | |
| 4,244,948 A | 1/1981 | Boghosian et al. | |
| 4,376,768 A | 3/1983 | Ozaki et al. | |
| 4,472,431 A | 9/1984 | Toth | |
| 4,543,353 A | 9/1985 | Faustini et al. | |
| 4,551,452 A | 11/1985 | Marfat | |
| 4,623,486 A | 11/1986 | Lombardino | |
| 4,640,689 A | 2/1987 | Sibalis | |
| 4,640,911 A | 2/1987 | Baschang et al. | |
| 4,689,338 A | 8/1987 | Gerster | |
| 4,743,704 A | 5/1988 | Nicolini | |
| 4,746,509 A | 5/1988 | Haggiage et al. | |
| 4,822,773 A | 4/1989 | Alexander et al. | |
| 5,081,118 A | 1/1992 | Braisted et al. | |
| 5,100,918 A | 3/1992 | Sunshine et al. | |
| 5,134,165 A | 7/1992 | Hirsch-Kauffmann | |
| 5,190,953 A | 3/1993 | Munson, Jr. et al. | |
| 5,192,753 A | 3/1993 | McGeer et al. | |
| 5,331,000 A | 7/1994 | Young et al. | |
| 5,399,562 A | 3/1995 | Becker et al. | |
| 5,570,559 A | 11/1996 | Lewis | |
| 5,604,259 A | 2/1997 | Jee | |
| 5,607,691 A | 3/1997 | Hale et al. | |
| 5,654,337 A | 8/1997 | Roentsch et al. | |
| 5,760,261 A | 6/1998 | Guttag | |
| 5,861,170 A | 1/1999 | Kissel | |
| 5,885,597 A | 3/1999 | Botknecht et al. | |
| 5,902,110 A | 5/1999 | Alfano et al. | |
| 5,981,591 A * | 11/1999 | Deihl | A61K 9/006 514/165 |
| 6,011,049 A | 1/2000 | Whitcomb | |
| 6,054,457 A | 4/2000 | Setoi et al. | |
| 6,190,690 B1 | 2/2001 | Park et al. | |
| 6,193,996 B1 | 2/2001 | Effing et al. | |
| 6,262,121 B1 | 7/2001 | Kawaji et al. | |
| 6,346,278 B1 | 2/2002 | Macrides et al. | |
| 6,368,618 B1 | 4/2002 | Jun et al. | |
| 6,416,772 B1 | 7/2002 | Van Engelen et al. | |
| 6,444,234 B1 | 9/2002 | Kirby et al. | |
| 6,528,040 B1 | 3/2003 | Pearson et al. | |
| 6,592,891 B1 | 7/2003 | Donati et al. | |
| 6,593,365 B1 | 7/2003 | Yung-Yu Hung et al. | |
| 6,635,674 B1 | 10/2003 | Kaneko et al. | |
| 6,638,528 B1 | 10/2003 | Kanios | |
| 6,693,135 B2 | 2/2004 | Yeager et al. | |
| 6,723,337 B1 | 4/2004 | Song et al. | |
| 6,773,724 B2 | 8/2004 | Franckowiak et al. | |
| 7,052,715 B2 | 5/2006 | Fishman | |
| 7,256,210 B2 | 8/2007 | Man et al. | |
| 2001/0038861 A1 | 11/2001 | Hsu et al. | |
| 2003/0087962 A1 | 5/2003 | Demopulos et al. | |
| 2004/0022837 A1 | 2/2004 | Hsu et al. | |
| 2004/0229920 A1 | 11/2004 | Garvey et al. | |
| 2004/0254182 A1 | 12/2004 | Mulvihill et al. | |
| 2004/0266870 A1 | 12/2004 | Allegretii et al. | |
| 2005/0037922 A1 | 2/2005 | Bickers et al. | |
| 2005/0049255 A1 | 3/2005 | Bictash et al. | |
| 2005/0080067 A1 | 4/2005 | Allegretii et al. | |
| 2005/0107463 A1 | 5/2005 | Woodward et al. | |
| 2005/0272108 A1 | 12/2005 | Kalra et al. | |
| 2006/0003428 A1 | 1/2006 | Tsai | |
| 2006/0024365 A1 | 2/2006 | Vaya et al. | |
| 2006/0172002 A1 | 8/2006 | Takada et al. | |
| 2007/0142607 A1 | 6/2007 | Harasin et al. | |
| 2008/0166413 A1 * | 7/2008 | Staniforth | A61K 9/2013 424/489 |

FOREIGN PATENT DOCUMENTS

| | | | |
|---|---|---|---|
| CA | 2614312 A1 | 1/2007 | |
| DE | 3023206 A1 | 1/1982 | |
| EP | 152379 A2 | 8/1985 | |
| EP | 0202062 A2 | 11/1986 | |
| EP | 237495 A2 | 9/1987 | |
| EP | 289262 A2 | 11/1988 | |
| EP | 0208404 B1 | 8/1990 | |
| EP | 0469450 A1 | 5/1992 | |
| EP | 0659442 A1 | 6/1995 | |
| FR | 5342 | 9/1967 | |
| FR | 1593024 A | 5/1970 | |
| FR | 2410641 A1 | 6/1979 | |
| GB | 958186 | 5/1964 | |
| GB | 984471 | 2/1965 | |
| GB | 1000208 | 8/1965 | |
| GB | 1165300 | 9/1969 | |
| GB | 1187259 | 4/1970 | |
| GB | 2154585 | 9/1985 | |
| JP | 57-183738 | 11/1982 | |
| JP | 2004-525112 | 8/2004 | |
| JP | 2005-504121 | 2/2005 | |
| WO | WO 1990/02141 A1 | 3/1990 | |
| WO | WO 1990/08128 | 7/1990 | |
| WO | WO 1993/07902 | 4/1993 | |
| WO | WO 1993/14743 A2 | 8/1993 | |
| WO | WO 1993/17677 A1 | 9/1993 | |
| WO | WO 93/25197 | 12/1993 | |
| WO | WO 1993/25703 A1 | 12/1993 | |
| WO | WO 1994/00449 | 1/1994 | |
| WO | WO 1994/10167 | 5/1994 | |
| WO | WO 1994/20635 A1 | 9/1994 | |
| WO | WO 1995/34813 | 12/1995 | |
| WO | WO 1996/028144 | 9/1996 | |
| WO | WO 1997/44020 A1 | 11/1997 | |
| WO | WO-9744020 A1 * | 11/1997 | A61K 31/167 |
| WO | WO 1997/45113 A1 | 12/1997 | |
| WO | WO 1998/040061 | 9/1998 | |
| WO | WO 1998/47502 A1 | 10/1998 | |
| WO | WO 01/54481 | 8/2001 | |
| WO | WO 2001/58852 A2 | 8/2001 | |
| WO | WO 2001/85143 A2 | 11/2001 | |
| WO | WO 2002/000167 A2 | 1/2002 | |
| WO | WO 2002/68377 A1 | 9/2002 | |
| WO | WO 2002/85297 A2 | 10/2002 | |
| WO | WO 2003/022270 A1 | 3/2003 | |
| WO | WO 2003/29187 A1 | 4/2003 | |
| WO | WO 2003/061713 A1 | 7/2003 | |
| WO | WO 2004/000300 | 12/2003 | |
| WO | WO 2004/004648 | 1/2004 | |
| WO | WO 2005/68421 A1 | 7/2005 | |
| WO | WO 2005/97099 A1 | 10/2005 | |
| WO | WO 2006/74249 A1 | 7/2006 | |
| WO | WO 2006/128184 A2 | 11/2006 | |
| WO | WO 2008/007171 A1 | 1/2008 | |
| WO | WO 2008/010025 A1 | 1/2008 | |
| WO | WO 2008/012602 A1 | 1/2008 | |
| WO | WO 2008/012603 A1 | 1/2008 | |
| WO | WO 2008/012605 A1 | 1/2008 | |

(56) References Cited

FOREIGN PATENT DOCUMENTS

| WO | WO 2008/017903 A1 | 2/2008 |
|---|---|---|
| WO | WO 2008/020270 A1 | 2/2008 |
| WO | WO 2008/026776 | 3/2008 |
| WO | WO 2008/029199 A1 | 3/2008 |
| WO | WO 2008/029200 A1 | 3/2008 |
| WO | WO 2008/041054 A1 | 4/2008 |
| WO | WO 2008/041059 A1 | 4/2008 |
| WO | WO 2008/044095 A1 | 4/2008 |
| WO | WO 2008/056207 A1 | 5/2008 |
| WO | WO 2008/072032 A1 | 6/2008 |
| WO | WO 2008/087493 A1 | 7/2008 |
| WO | WO 2008/093173 A1 | 8/2008 |
| WO | WO 2008/149181 A1 | 12/2008 |
| WO | WO 2008/021605 A1 | 1/2009 |

OTHER PUBLICATIONS

Patani et al. "Bioisosterism: A Rational Approach in Drug Design", Chem. Rev., 1996, vol. 96, pp. 3147-3176. (Year: 1996).*

Engilish machine translation of FR 4672 on Mar. 18, 2019 (Year: 2019).*

Agawa, T., et al., "Stabilities of Vitamin A Urethans," Kogyo Kagaku Zasshi 58:686-688 (1955).

Allegretti, M. et al., "2-Arylpropionic CXC Chemokine Receptor 1 (CXCR1) Ligands as Novel Noncompetitive CXCL8 Inhibitors," J. Medic. Chem. 48(13):4312-4331 (2005).

Altuntas, T. G., et al., "A Study on the Interation Between p60c-src Receptor Tyrosine Kinase and Arylcarboxylic and Arylacetic Acid Derivatives Based on Docking Modes and In Vitro Activity," Biol. Pharm. Bull. 27(1):61-65 (2004).

Amin, R. C., et al., "Diethylaminoethyl Dialkylacetates," J. Amer. Pharma. Association 37:243-245 (1948).

Andrews, J. M., "Determination of Minimum Inhibitory Concentrations," Journal of Antimicrobial Chemotherapy 48, suppl. S1: 5-16 (2001).

Apt, L., et al., "A Randomized Clinical Trial of the Nonsteroidal Eyedrop Diclofenac After Strabismus Surgery," Ophthalmology 105:1448-1454 (1998).

Arora, P., et al., "Design Development, Physicochemical, and In Vitro and In Vivo Evaluation of Transdermal Patches Containing Diclofenac Diethylammonium Salt," J. Pharm. Sci. 91:2076-2089 (2002).

Barcia, E., et al., "Influence of Medium and Temperature on the Hydrolysis Kenetics of Propacetamol Hydrochloride: Determination Using Derivative Spectrophotometry," Chem. Pharm. Bull. 53(3):277-280 (2005).

Battaglino, R., et al., "Fluoxetine Treatment Increases Trabecular Bone Formation in Mice (Fluoxetine Affects Bone Mass)," J. Cell Biochem. 100(6):1387-1394 (2007).

Berge, S. M., et al., "Pharmaceutical Salts," J. Pharm. Sci. 66:1-19 (1977).

Brown, K., et al., "Nonsteroidal Antiinflammatory Agents. 1.2,4-Diphenylthiazole-5-acetic Acid and Related Compounds," J. Med. Chem.17(11):1177-1181 (1975).

Bundgaard, H., et al., "Prodrugs as Drug Delivery Systems IV: N-Mannich Bases as Potential Novel Prodrugs for Amides, Ureides, Amines, and Other NH-Acidic Compounds," J. Pharm. Sci. 69:44-46 (1980).

Campbell, C. L., et al., "Aspirin Dose for the Prevention of Cardiovascular Disease," JAMA 297(18):2018-2024 (2007).

Carrico, D., et al., "In Vitro and In Vivo Antimalarial of Peptidomimetic Protein Farnesyltransferase Inhibitors with Improved Membrane Permeability," Bioorg. Med. Chem. 12(24):6517-6526 (2004).

Cevc, G., et al., "New, Highly Efficient Formulation of Diclofenac for the Topical, Transdermal Administration in Ultradeformable Drug Carriers, Transfersomes," Biochim. Biophys. Acta 1514:191-205 (2001).

Chanal, J. L., et al., "Etude de la Distribution et de L'Elimination Chez le Rat de L'Acetyl Salicylate de Dimethyl Amino Ethyle Influence de la Position du Marquage au Carbone 14," Boll. Chim. Farm. 119:331-338 (1980).

Cwalina, G. E., et al., "Synthesis and Stability Studies of Certain Disubstituted Aminoacetoxybenzoic Acids," J. Organic Chem. 26:3344-3346 (1961).

Dalpiaz, A., et al., "Vitamin C and 6-Amino-Vitamin C Conjugates of Diclofenac: Synthesis and Evaluation," International Journal of Pharmaceutics 291(1-2):171-181 (2005).

D'Amour, F. E., et al., "A Method for Determining Loss of Pain Sensation," J. Pharmacol. Exp. Ther. 72:74-79 (1941).

Diven, W. F., et al., "Treatment of Experimental Acute Otitis Media with Ibuprofen and Ampicillin," Int. J. Pediatric Otorhinolaryngology 33:127-139 (1995).

Drachman, D. B., et al., "Cyclooxygenase 2 Inhibition Protects Motor Neurons and Prolongs Survival in a Transgenic Mouse Model of ALS," Ann. Neurol. 52:771-778 (2002).

Erlanson-Albertsson, C., et al., "Enterostatin—A Peptide Regulating Fat Intake," Obes. Rev. 5(4):360-372 (1997).

Funt, L. S., "Oral Ibuprofen and Minocycline for the Treatment of Resistant Acne Vulgaris," J. Amer. Acad. Dermatol. 13(3):524-525 (1985).

Gamache, D.A., et al., "Nepafenac, A Unique Nonsteroidal Prodrug with Potential Utility in the Treatment of Trauma-Induced Ocular Inflammation: I. Asssessment of Anti-Inflammatory Efficacy," Inflammation 24(4):357-370 (2000).

Gidoh, M., et al., "Derivatives of Several Acidic Anti-Inflammatory Drugs Showing Local Anesthetic Effects and Their Possible Use in the Treatment of Leprous Neuritis," Nippon Rai Gakkai Zasshi 52(3):156-64 (1983).

Ginaldi, L., et al., "Osteoporosis, Inflammation and Ageing," Immunity & Ageing 2:14 (2005).

Giraud, I., et al., "Application to a Cartilage Targeting Strategy: Synthesis and In Vivo Biodistribution of 14C-Labeled Quaternary Ammonium-Glucosamine Conjugates," Bioconjugate Chem. 11:212-218 (2000).

Gossel, T.A., "Aspirin's Role in Reducing Cardiac Mortality," U.S. Pharmacitst, Feb. 1988, pp. 34-41.

Gringauz, A., "Certain Disubstituted O-Aminoacetoxy- and Propoxybenzoic and Cinnamic Acids and Their Tert-Butyl Esters," J. Pharma. Sci. 59(3):422-225 (1970).

Hacking, M.A.P.J., et al., "Lipase Catalysed Acylation of Hydroxylamine and Hydrazine Derivatives," Journal of Molecular Catalysis B: Exzymatic 11:315-321 (2001).

Halen, P. K., et al., "Combining Anticholinergic and Anti-Inflammatory Activities into a Single Moiety: A Novel Approach to Reduce Gastrointestinal Toxictiy of Ibuprofen and Ketoprofen," Chem. Bioi. Drug Des. 70:450-455 (2007).

Halen, P. K., et al., "Synthesis and Pharmacological Evaluation of Some Dual-Acting Amino-Alcohol Ester Derivatives of Flurbiprofen and 2-[1, 1'-Biphenyl-4-yi]Acetic Acid: A Potential Approach to Reduce Local Gastrointestinal Toxicity," Chemistry & Biodiversity 3(11 ):1238-1248 (2006).

Hengesh, E. J., Principles of Medicinal Chemistry, 4th Ed., p. 591, Williams & Wilkins, 1995.

Hennekens, C. H., et al., "Final Report on the Aspirin Component of the Ongoing Physicians' Health Study," N. Eng. J. Med. 321:129-135 (1989).

Horan, P. J., et al., "Antinociceptive Profile of Biphalin, a Dimeric Enkephalin Analog," J. Pharmacology & Experimental Therapeutics 265(3): 1446-1454 ( 1993).

Hovgaard, L., et al., "Drug Delivery Studies in Caco-2 Monolayers. Synthesis, Hydrolysis, and Transport of O-Cyclopropane Carboxylic Acid Ester Prodrugs of Various B-Biocking Agents," Pharm. Res. 12(3):387-392 (1995).

Hovgaard, L., et al., "Permeation Studies on O-Cyclopropanoyl Ester Prodrugs of B-Biockers in Caco-2 Cell Monolayers," Proceed. Intern: Symp. Control. Rei. Bioacl. Mater. 20:238-239 (1993).

In't Veld, B. A., et al., "Nonsteroidal Antiinflammatory Drugs and the Risk of Alzheimer's Disease," N. Eng. J. Med. 345(21):1515-1521 (2001).

(56) References Cited

OTHER PUBLICATIONS

Jona, J. A., et al., "Design of Novel Prodrugs for the Enhancement of the Transdermal Penetration of Indomethacin," International Journal of Pharmaceuticals 123:127-136 (1995).

Jung, Y. J., et al., "Colon-Specific Prodrugs of 5-Aminosalicylic Acid: Synthesis and In Vitro/In Vivo Properties of Acidic Amino Acid Derivatives of 5-Aminosalicylic Acid," J. Pharm. Sci. 90:1767-1775 (2001).

Kawathekar, N., et al., "Synthesis, Biological Evaluation and QSAR Analysis of Some New Derivatives of Ketoprofen and Flurbiprofen," Indian J. Pharma.ceutical Sciences 60(6):346-352 (1998).

Kigasawa, K., et al., "Decomposition and Stabilization of Drugs. XVIII. Studies on the Stability of Carboxylic Acid Esters of Phenol and Their Effectiveness as Prodrug," J. Pharm. Soc. Japan 99(4):402-412 (1979).

Kisel, V.M., et al., "Condensed Isoquinolines. 15. Synthesis of 5,10-Dihydro[1,2,4]Triazolo[1,5-b]-Isoquinolines and Related Spiranes," Chemistry of Heterocyclic Compounds 38(10):1253-1262 (2002).

Knychalska-Karwan, Z., et al., "The Use of Edan in Stomatodynia," J. Stomatal. 38:10 (1985).

Kobayashi, M., et al., "A Model System for Convenient Fluorescent Labeling of Sugar Chain in Taka-Amylase A.," Biosci. Biotechnol. Biochem. 61(11):1836-1839 (1997).

Korean Intellectual Property Office, International Preliminary Report on Patentability for PCT/IB2006/052318 dated May 7, 2007.

Korean Intellectual Property Office, International Preliminary Report on Patentability for PCT/IB2006/052461 dated Mar. 29, 2007.

Korean Intellectual Property Office, International Preliminary Report on Patentability for PCT/IB2006/052549 dated Apr. 23, 2007.

Korean Intellectual Property Office, International Preliminary Report on Patentability for PCT/IB2006/052563 dated Apr. 25, 2007.

Korean Intellectual Property Office, International Preliminary Report on Patentability for PCT/IB2006/052575 dated Apr. 25, 2007.

Korean Intellectual Property Office, International Preliminary Report on Patentability for PCT/IB2006/053090 dated May 12, 2007.

Korean Intellectual Property Office, International Preliminary Report on Patentability for PCT/IB2006/053594 dated Jun. 20, 2007.

Korean Intellectual Property Office, International Preliminary Report on Patentability for PCT/IB2006/053619 dated Jun. 26, 2007.

Korean Intellectual Property Office, International Preliminary Report on Patentability for PCT/IB2006/053091 dated May 12, 2007.

Korean Intellectual Property Office, International Preliminary Report on Patetability for PCT/IB2007/052090 dated May 31, 2007.

Korean Intellectual Property Office, International Preliminary Report on Patentability for PCT/US2009/066884 dated Jun. 7, 2011.

Korean Intellectual Property Office, International Search Report for PCT/IB2006/052732 dated May 2, 2007.

Korean Intellectual Property Office, International Search Report for PCT/IB2006/052815 dated May 3, 2007.

Korean Intellectual Property Office, International Search Report for PCT/IB2006/053741 dated May 29, 2007.

Kovach, I. M., et al., "Amino Acid Esters of Phenols as Prodrugs: Synthesis and Stability of Glycine, beta-Aspartic Acid, and alpha-Aspartic Acid Esters of p-Acetamidophenol," J. Pharm. Sci. 70(8):881-885 (1981).

Machon, Z., et al., "Synthesis of Benzoylcholine Derivatives," Dissertationes Pharmaceuticae 17(4):491-496 (1965).

Madhu, C., et al., "Penetration of Natural Prostaglandins and Their Ester Prodrugs and Analogs Across Human Ocular Tissues in Vitro," Journal of Ocular Pharmacology 14(5):389-399 (1998).

Magnette, J.-L., et al., "Diclofenac Systemic Exposure is Not Increased when Topical Diclofenac is Applied to Ultraviolet-Induced Erythema," Eur. J. Clin. Pharmacol. 60:591-594 (2004).

McGeer, P.L., et al., "The Inflammatory Response System of Brain Implications for the Theray of Alzheimer and Other Neurodegenerative Diseases," Res. Rev. 21:195-218 (1995).

Milosovich, S., et al., "Testosteronyl-4-Dimethylaminobutyrate-HCl: A Prodrug with Improved Skin Penetration Rate," J. Pharm. Sci. 82(2):227-228 (1993).

Nebioglu, D., et al., "Synthesis and In Vitro Anti-Inflammatory Activities of Some New Diaryl Amine Derivatives as Prodrug of Diclofenac," J. Fac. Pharm. Gazi 10(1):69-81 (1993).

Nicolas, C., et al., "New Quaternary Ammonium Oxican Derivatives Targeted Toward Cartilage: Synthesis, Pharmacokinetic Studies, and Antiinflammatory Potency," J. Med. Chem. 42:5235-5240 (1999).

Nielsen, N. M., et al., "Evaluation of Glycolamide Esters and Various Other Esters of Aspirin as True Aspirin Prodrugs," J. Med. Chem. 32(3):727-734 (1989).

Non_steroidal_antiinflammatory_dr,2011, http://en.wikipedia.org/wiki/Non-steroidal_anti-inflammatory_drug.

Pan, D.S., et al., "Inhibitory Effect of Progesterone on Inflammatory Factors after Experimental Traumatic Brain Injury," Biomed. Environ. Sci. 20(5):432-438 (2007).

PDR Generics, "Fenoprofen Calcium," 1996, second edition, Medical Economics, Montvale, NJ, p. 1289-1292.

PDR Generics, "Ketoprofen," 1996, second edition, Medical Economics, Montvale, NJ, p. 1810-1815.

PDR Generics, 1996, 2nd Ed., Medical Economics, Montvale, New Jersey, p. 242-243.

Perioli, L., et al., "Potential Prodrugs of Non-Steroidal Anti-Inflammatory Agents for Targeted Drug Delivery to the CNS," European Journal of Medicinal Chemistry 39(8):715-727 (2004).

Ponte, C., et al., "Does Acetaminophen Interfere in the Antibiotic Treatment of Acute Otitis Media Caused by a Penicillin-Resistant Pneumococcus Strain? A Gerbil Model," Pediatric Res. 54(6):913-918 (2003).

Raisz, L., "Pathogenesis of Osteoporosis: Concepts, Conflicts, and Prospects," J. Clin. Invest. 115(12):3318-3325 (2005).

Rolka, D. B., et al., "Aspirin Use Among Adults with Diabetes," Diabetes Care 24(2):197-201 (2001).

Romundstad, L., et al., "Adding propacetamol to Ketorolac Increase the Tolerance to Painful Pressure," European Journal of Pain (Amsterdam, Netherlands) 10(3):177-183, ISSN:1090-3801 (2006).

Roof, R.L., et al., "Gender Differences in Acute CNS Trauma and Stroke: Neuroprotective Effects of Estrogen and Progesterone," J. Neurotrauma 17(5):367-388 (2000).

Rosenberg, E.W., et al., "Effect of Topical Applications of Heavy Suspensions of Killed Malassezia Ovalis on Rabbit Skin," Mycopathologia 72:147-154 (1980).

Roth, H. J., et al., "Synthesis of Polymer Bound Antiphlogistic Agents," Archiv der Pharmazie 321(5):273-276 (1988).

Salimbeni, A., et al., "New Esters of N-Arylanthranilic Acids," Farmaco, Edizione Scientifica 30(4):276-286 (1975).

Santos, C., et al., "Cyclization-Activated Prodrug. Synthesis, Reactivity and Toxicity of Dipeptide Esters of Paracetamol," Bioorganic & Medicial Chemistry Letters 15(6):1595-1598 (2005).

Scott, I. L., "Keystone Symposia: Inflammation and Cancer, Breckenridge, CO, USA, Feb. 27-Mar 3, 2005," Technical Reports 10(13)1-17.

Selim, A. S. M., et al., "A New Method for the Direct Isolation of Glycine from Protein Hydrolyzates," Biochemical Journal 61(2):177-179 (1955).

Shanbhag, V. R., et al., "Ester and Amide Prodrugs of Ibuprofen and Naproxen: Synthesis, Anti-Inflammatory Activity, and Gastrointestinal Toxicity," Journal of Pharmaceutical Sciences 81(2):149-54 (1992).

Silverman, R.B., "The Organic Chemistry of Drug Design and Drug Action," Academic Press Inc. 1992, pp. 355-361.

Sloan, K. B., et al., "Design for Optimized Topical Delivery: Prodrugs and a Paradigm Change," Pharmaceutical Research 23(12):2729-2747 (2006).

Sloan, K. B., et al., "Designing for Topical Delivery: Prodrugs Can Make the Difference," Medicinal Research Reviews 23(6):763-793 (2003).

Soine, T. O., et al., "Antispasmodics. I. Phenyl Esters of Beta-Dialkylaminopropionic Acids," J. Am. Pharm. Assoc. 41:236-238 (1952).

Song, N., et al., "Synthesis of a Derivative of Quaternary Ammonium-Ibuprofen," Journal of Ocean University of Qingdao 32(6):911-913 (2002).

(56) References Cited

OTHER PUBLICATIONS

Sorhede, M., et al., "Enterostatin: A Gut-Brain Peptide Regulating Fat Intake in Rat," J. Physiol. 87:273-275 (1993).

SpinalCordinjury,2011, http://www.mayoclinic.com/health/spinal-cord-injury/DS00460/DSECTION=treatments-and-drugs.

Terry, M. B., et al., "Association of Frequency and Duration of Aspirin Use and Hormone Receptor Status With Breast Cancer Risk," JAMA 291(21):2433-2489 (2004).

Thun, M.J., et al., "Aspirin Use and Reduced Risk of Fatal Colon Cancer," N. Eng. J. Med., 325(23):1593-1596 (1991).

Tjebbes, G.W.A., et al., "d-Ibuprofen in Ocular Inflammation Induced by Paracentesis of the Rabbit Eye," Prostaglandins, Butterworth, Stoneham, MA, US 40(1):29-33 (1990).

Toyooka, T., et al., "Fluoroescent Chiral Derivatization Reagents for Carboxylic Acid Enantiomers in High-Performance Liquid Chromatography," Caplus an 1992:523750 (1992).

Tozkoparan, B., et al.,"6-Benzylidenethiazolo[3,2-b]-1,24-Triazole-5(6H)-Ones Sybstituted with Ibprofen: Synthesis, Characterization and Evaluation of Anti-Inflammatory Activity," Eur. J. Med. Chem. 35(7-8):743-750 (2000).

Tute, M. S., et al., Principles of Medicinal Chemistry, Eds., Williams & Wilkins, Media, PA, 1995, pp. 52.

Urbanska, H., et al., "Synthesis and Pharmacological Properties of Aminoalkyl Esters of Nicotinic Acid Derivatives," Acta Poloniae Pharmaceutica 36(6):657-665 (1979).

Venuti, M. C., et al., "Synthesis and Biological Evaluation of Omega-(N,N,N-Trialkylammonium)Alkyl Esters and Thioesters of Carboxylic Acid Nonsteroidal Antiinflammatory Agents," Pharmaceutical Research 6(10):867-873 (1989).

Warolin, C., et al., "Sur L'Activite Pharamacodynamique de L'Anhydride Acetylsalicylique et du Chlorhydrate D'Acetylsalicylate de N Diethylaminoethyle (1)," Therapie 21(1):245-59 (1966).

Wiwattanawongsa, K., et al., "Experimental and Computational Studies of Epithelial Transport of Mefenamic Acid Ester Prodrugs," Pharmaceutical Research 22(5):721-727 (2005).

Wolinski, J., et al., "Search for Anticholinargic Compounds. XX. Synthesis of Aminoalkyl O-, M-, and P-Hydroxybenzoates and O-, M-, and P-Acetoxybenzoates," Acta Poloniae Pharmaceutica 37(3):275-280 (1980).

Woods, H. F., et al., "Inhibition by Salicylate of Gluconeogenesis in the Isolated Perfused Rat Liver," Clin. Exp. Pharmacol. Physiol. 1(6):535-540 (1974).

Wright, D.W., et al., "ProTECT: A Randomized Clinical Trial of Progesterone for Acute Traumatic Brain Injury," Ann. Emerg. Med. 49(4):391-402 (2007).

Xiao, G., et al., "Improved Outcomes from the Administration of Progesterone for Patients with Acute Severe ttraumatic bbrain iinjury: A Randomized Controlled Trial," Crit. Care 12:R61 (2008).

Yadav, M.R., et al., "Synthesis and Pharmacological Evaluation of Some Dual-Acting Aminoalcohol Ester Derivatives of Flurbiprofen and 2-[1,1'-Biphenyl-4-yl] Acetic Acid: A Potential Approach to Reduce Local Gastrointestinal Toxicity," Chem. & Biodiversity 3(11):1238-1248 (2006).

Yang, S., et al., "Specificity of RGS10A as a Key Component in the RANKL Signaling Mechanism for Osteoclast Differentiation," J. Cell Sci. 120:3362-3371 (2007).

Zovko, M., et al., "Macromolecular Prodrugs. IX. Synthesis of Polymer-Fenoprofen Conjugates," Int. J. Pharmaceutics 228:129-138 (2001).

Zovko, M., et al., "The Novel Ketoprofenamides: Synthesis and Spectroscopic Characterization," Croatica Chemica Acta 76(4):335-341 (2003).

J.G. Cannon "Analog Design", Chaper Ninteen in Burger's Medicinal Chemistry and Drug Discovery, Fifth Edition, vol. I; Principles and Practice, Wiley-Interscience 1995, pp. 783-802, 784.

Ho et al. "The percutaneous penetration of prostaglandin E1 and its alkyl esters" Journal of Controlled Release, 1999, vol. 58, pp. 349-355.

Database Caplus [Online] Chemical Abstracts Service, Columbus, OH, US; "Esters of .omega.-aminoaliphatic Acids and p-acetamidophenol," retrieved from STN database accession No. 1969:3537 (one page).

Foye, W. O., et al., Principles of Medicinal Chemistry, 4th Ed., Williams & Wilkins, p. 549 (1995) (three pages).

* cited by examiner

HIGH PENETRATION COMPOSITION AND USES THEREOF

PRIORITY CLAIM

The present application is a divisional of U.S. application Ser. No. 12/397,308, filed Mar. 3, 2009, which is a continuation-in-part application of International Application PCT/IB2006/053091, with an international filing date of Sep. 3, 2006, and designating the U.S.; and a continuation-in-part application of U.S. application Ser. No. 12/351,804, filed on Jan. 9, 2009, both of which are incorporated herein by reference in their entirety. Application Ser. No. 12/397,308 also claims priority to U.S. Provisional Application 61/120,052, filed Dec. 4, 2008, which is incorporated herein by reference in its entirety. The U.S. application Ser. No. 12/351,804, filed on Jan. 9, 2009, is a continuation-in-part application of International Application PCT/IB2006/052318, with an international filing date of Jul. 9, 2006; a continuation-in-part application of International Application PCT/IB2006/052461, with an international filing date of Jul. 18, 2006; a continuation-in-part application of International Application PCT/IB2006/052549, with an international filing date of Jul. 25, 2006; a continuation-in-part application of International Application PCT/IB2006/052563, with an international filing date of Jul. 26, 2006; a continuation-in-part application of International Application PCT/IB2006/052575, with an international filing date of Jul. 27, 2006; a continuation-in-part application of International Application PCT/IB2006/052732, with an international filing date of Aug. 8, 2006; a continuation-in-part application of International Application PCT/IB2006/052815, with an international filing date of Aug. 15, 2006; a continuation-in-part application of International Application PCT/IB2006/053090, with an international filing date of Sep. 3, 2006; and a continuation-in-part application of International Application PCT/IB2006/053741, with an international filing date of Oct. 11, 2006; and designating the U.S., all of which are incorporated herein by reference in their entirety.

FIELD OF THE INVENTION

This invention relates to the field of pharmaceutical compositions and methods of using the pharmaceutical compositions for penetrating one or more biological barriers, treating conditions, diagnosing conditions or screening for new compositions.

BACKGROUND

Active agents or drugs that are effective in vitro may not be as effective in vivo due to the delivery difficulties in vivo, in particular, their limited penetration ability across one or more biological barriers (BBs) before reaching the site of action where diseases occur in vivo.

Currently many drugs are administered through systematic route, such as oral or parenteral administration, to reach the action site of a condition or disease. Since a higher dosage of a drug is required to reach a distal location in the systematic administration, drugs delivered by such a route may cause adverse reactions. For example, 4-aminophenol derivatives (e.g. acetaminophen (N-acetyl-p-aminophenol)) have been used as analgesic and antipyretic drugs. Although acetaminophen is used to relieve fever as well as the signs and symptoms of rheumatoid arthritis and osteoarthritis, a number of side effects are associated with the use of acetaminophen and the related compounds. The side effects include hepatotoxicity and nephrotoxicity in humans and in experimental animals. Acute overdosage of acetaminophen may result in dose-dependent and potentially fatal hepatic necrosis as well as renal tubular necrosis and hypoglycemia.

Modifications of the known drugs have been reported to improve their efficacy and decrease their side effects. Fishman and many others (Fishman; Robert, U.S. Pat. No. 7,052,715; Van Engelen et al. U.S. Pat. No. 6,416,772; Macrides et al. U.S. Pat. No. 6,346,278; Kirby et al. U.S. Pat. No. 6,444,234, Pearson et al. U.S. Pat. No. 6,528,040, and Botknecht et al. U.S. Pat. No. 5,885,597) have attempted to develop a delivery system for transdermal application by drug formulation to reduce the side effects associating with oral administration and achieve localized drug administrations with reduced systematic exposure. However, to treat a condition at distal areas, a much higher plasma concentration of the active agent is required when the drug is administered orally than when the drug is administered at the particular site of the condition. It is very difficult, however, to deliver therapeutically effective plasma levels of these drugs by the known formulations.

Therefore, there is a need to develop novel compositions and methods that are capable of delivering an active agent efficiently and effectively to an action site of a condition (e.g., a disease) to prevent, reduce or treat the condition and minimize side effects.

SUMMARY OF THE INVENTION

One aspect of the invention relates to a high penetration prodrug (HPP) or a high penetration composition (HPC) comprising a functional unit covalently linked to a transportational unit through a linker.

In certain embodiments, the functional unit comprises a moiety of an agent wherein the delivery of the agent into a biological subject or transportation across a biological barrier (BB) is desired. In certain embodiments, the agent comprises an active agent or an agent that can be metabolized into an active agent or active metabolite.

In certain embodiments, the functional unit may be hydrophilic, lipophilic, or amphiphilic (hydrophilic and lipophilic). For example, the lipophilic nature of the function unit may be inherent or achieved by converting its hydrophilic moieties to lipophilic moieties.

In certain embodiments, the functional unit of a HPP or HPC comprises a moiety of an agent wherein the agent is a 4-aminophenol derivative, an active 4-aminophenol derivative metabolite or an agent that can be metabolized into a 4-aminophenol derivative or 4-aminophenol derivative metabolite after the HPP or HPC penetrates one or more BBs. Examples of 4-aminophenol derivatives include, but are not limited to, N-acetyl-p-aminophenol (acetaminophen), 4-acetamidophenyl salicylate (acetaminosalol) and related compounds.

In certain embodiments, the transportational unit of a HPP or HPC comprises a protonatable amine group that is capable of facilitating the transportation or crossing of the HPP through one or more biological barriers. In certain embodiments, the protonatable amine group is substantially protonated at the pH of the BBs the HPP penetrates through. In certain embodiment, the amine group can be reversibly protonated.

In certain embodiments, the linker covalently linking the functional unit and the transportational unit comprises a bond that is capable of being cleaved after the HPP penetrates across one or more BBs. The cleavable bond comprises, for example, a covalent bond, an ether, thioether, amide, ester, thioester, carbonate, carbamate, phosphate or oxime bond.

Another aspect of the invention relates to a pharmaceutical composition comprising one HPP and a pharmaceutically acceptable carrier (HPP composition).

Another aspect of the invention relates to the use of a HPC or HPP of the invention in penetrating a biological barrier by applying the HPC or HPP to the biological barrier.

Another aspect of the invention relates to methods for screening a test functional unit, a test linker, or a test transportational unit with desired characters.

Another aspect of the invention relates to methods for preventing, ameliorating, or treating a condition in a biological subject by administering a composition of the present invention. In certain embodiments, the method relates to treating a condition treatable by a 4-aminophenol derivative (e.g. fever, pain, rheumatoid arthritis and osteoarthritis) by administering a HPP or HPC of a 4-aminophenol derivative.

Another aspect of the invention relates to administration of a HPP or HPC to a subject in need thereof. In certain embodiments, the composition of the present invention is administrated to a biological subject through various delivery routes such as oral, enteral, buccal, nasal, topical, rectal, vaginal, aerosol, transmucosal, epidermal, transdermal, dermal, ophthalmic, pulmonary, subcutaneous, and/or parenteral administration. In certain embodiments, the composition of the present invention is administered orally, transdermally, topically, subcutaneously and/or parenterally.

Another aspect of the invention relates to the advantages of HPP or HPC according to the present invention. The advantages include, for example, local administration of a HPP or HPC to a site of condition with less dosage but higher concentration, avoidance of systematic administration and reduction of adverse effects (e.g., pain of injection, gastrointestinal/renal effects, and other side effect), possible novel treatment due to high local concentration of the HPP or active agent derived thereof. The advantages further include, for example, systematic administration of a HPP to a biological subject to achieve faster and more efficient bioavailability, penetration of biological barriers (e.g., the blood brain barrier) which have been difficult to cross, and new indications as a result of passing through biological barriers.

EXEMPLARY EMBODIMENTS OF THE INVENTION

Figure 1:
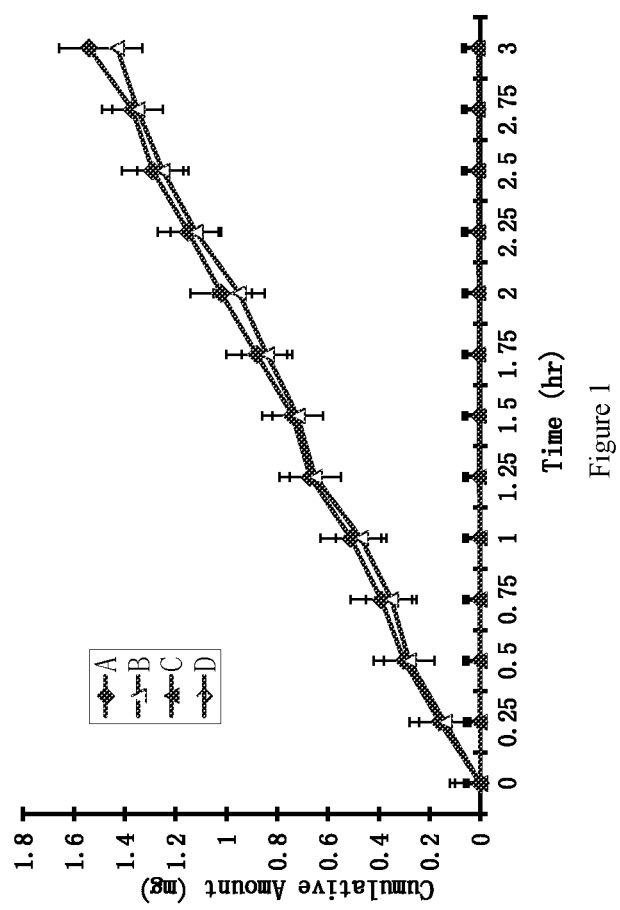
FIG. 1: Cumulative amounts of N-acetyl-p-aminophenyl dimethylaminobutyrate.HCl (A, 20% solution), 4-acetamidophenyl salicylyl dimethylaminobutyrate.HCl (B, 20% solution), N-acetaminophen (C, 20% suspension), and 4-acetamidophenyl salicylate (D, 20% suspension) crossing isolated human skin tissue in Franz cells (n=5). In each case, the vehicle was pH 7.4 phosphate buffer (0.2 M).

I. Structure of High Penetration Prodrug (HPP) or High Penetration Composition (HPC)

One aspect of the invention relates to a high penetration prodrug (HPP) or a high penetration composition (HPC). The term "high penetration prodrug" or "HPP" or "high penetration composition" or "HPC" as used herein refers to a composition comprising a functional unit covalently linked to a transportational unit through a linker. The functional unit comprises a moiety of an agent (e.g., a drug). The functional unit has properties including that 1) the delivery of the agent or the HPP into a biological subject or transportation across a biological barrier is desired, 2) the HPP is capable of penetrating or crossing a biological barrier, and 3) the HPP is capable of being cleaved so as to turn the moiety of the agent into an agent or active agent after cleavage. In certain embodiments, the agent of a HPP or HPC comprises an active agent or an agent that can be metabolized into an active agent or active metabolite.

In certain embodiments, a functional unit of a HPP or HPC may be hydrophilic, lipophilic, or amphiphilic (hydrophilic and lipophilic). A lipophilic moiety of a function unit may be inherent or achieved by converting one or more hydrophilic moieties of the functional unit to lipophilic moieties. For example, a lipophilic moiety of a functional unit is produced by converting one or more hydrophilic groups of the functional unit to lipophilic groups via organic synthesis. Examples of hydrophilic groups are carboxylic, hydroxyl, thiol, amine, phosphate/phosphonate and carbonyl groups. Lipophilic moieties produced via the modification of these hydrophilic groups are ethers, thioethers, esters, thioesters, carbonates, carbamates, amides, phosphates and oximes.

In certain embodiments, the agent of a HPP or HPC is a 4-aminopheno derivative, an active 4-aminophenol derivative metabolite, an agent that can be metabolized into a 4-aminophenol derivative or an active 4-aminophenol derivative metabolite after the HPP or HPC penetrates one or more BBs. The agent of the functional unit can be further converted to lipophilic moiety as described supra.

The term "4-aminophenol derivative" is a compound comprising the following structure A:

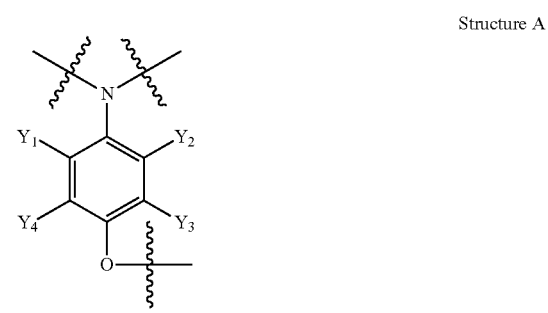

Structure A including stereoisomers and pharmaceutically acceptable salts thereof.

4-Aminophenol derivatives have analgesic and/or antipyretic effects. Examples of 4-aminophenol derivatives include, but are not limited to, N-acetyl-p-aminophenol (acetaminophen), 4-acetamidophenyl salicylate (acetaminosalol) and related compounds.

In one embodiment, the functional unit of a HPP of a 4-aminophenol derivative comprises a moiety having a structure selected from Group F-1, wherein Group F-1 includes the following structures:

Structure F-1a
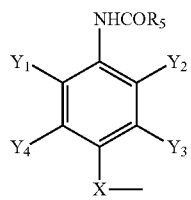

Structure F-1b
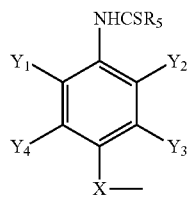

Structure F-1c
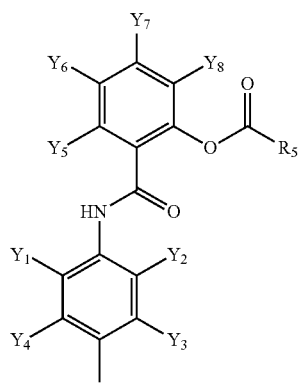

Structure F-1d
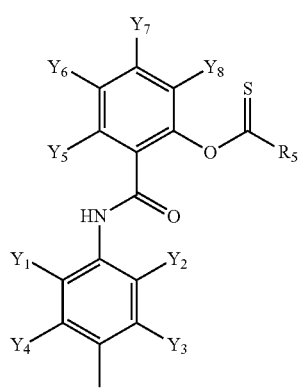

Structure F-1e
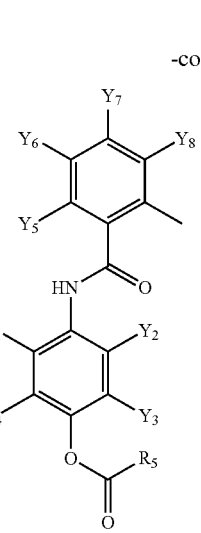

Structure F-1f
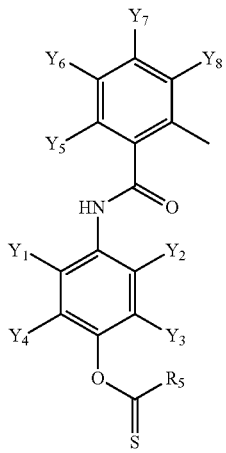

Structure F-1g
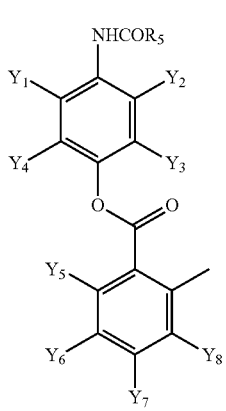

-continued

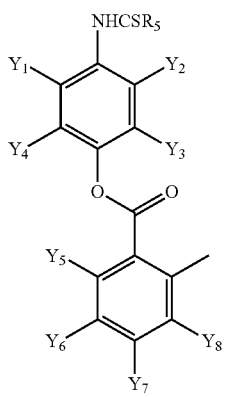

Structure F-1h including stereoisomers and pharmaceutically acceptable salts thereof.

As used herein, unless specified otherwise, each R and $R_1$-$R_6$ is independently selected from the group consisting of H, OH, Cl, F, Br, I, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, $P(O)OR_6$, CH=CH, C≡C, $CHR_6$, $CR_5R_6$, aryl, heteroaryl, and cyclic groups.

As used herein, unless specified otherwise, each $Y_1$ to $Y_8$ is independently selected from the group consisting of H, halogen, CN, $R_{10}$, $CH_3C$≡C, $CR_6$≡C, $P(O)OR_6$, $CF_3$, $CF_3O$, $CH_3$, $CF_3CF_2$, $CF_3CF_2O$, $CH_3CH_2$, $CH_3CH_2CH_2$, $(CH_3)_2CH$, $(CH_3)_2CHCH_2$, $CH_3CH_2CH(CH_3)$, $(CH_3)_3C$, $C_4H_9$, $C_5H_{11}$, $CH_3CO$, $CH_3CH_2CO$, $R_5CO$, $CH_3COO$, $R_5COO$, $R_5COOCH_2$, $R_6NHCOOCH_2$, $CH_3COS$, $CH_3O$, $R_5O$, HO, $R_{10}O$, $CF_3CH_2SCH_2$, $CHCl_2$, $CH_2COOR_6$, $CH_3S$, $R_5S$, HS, $R_{10}S$, $CH_3OCH_2CH_2$, $R_5OCH_2$, $R_{10}OCH_2CH_2$, $R_5O$ (C=O), $C_2H_5OCONH$, $CH_2NHR_8$, $CH_3OCONH$, $CH_3SO_2$, $CH_3SO$, $R_5SO_2$, $R_5SO$, $NH_2SO_2$, $C_6H_5CH_2$, $NH_2$, $NHR_{10}$, cyclobutyl, cyclopropyl, 4-chlorophenyl, 4-fluorophenyl, $CH_2$=CH, $CH_2$=CHCH$_2$, $CH_3CH$=CH, $NHR_5SO_2$, $N(R_5)_2SO_2$, $R_5OCH_2CH_2CH_2$, and $NO_2$.

As used herein, unless specified otherwise, each $R_{10}$ is independently selected from the group consisting of nothing, H, $R_6$, $R_6C$(=O)—, $R_6NH(C$=O), $R_6O(C$=O), $R_6C$ (=NH)—, $R_6C$(=S)—, $CNR_6$ and $R_6OCO(CH_2)_nC$(=O), wherein n is selected from the group of natural numbers. In certain embodiments, n is selected from the group of natural numbers of the range of 1-30. In certain embodiments, n is selected from the group of natural numbers of the range of 1-20. In certain embodiments, n is selected from the group of natural numbers of the range of 1-12.

As used herein, unless specified otherwise, X is selected from the group consisting of nothing, O, 2-OCO—$C_6H_4$— and 2-OCO—$C_6H_4$—O—CO—$C_6H_4$—, wherein each of the benzene ring can be further substituted by one or plural of the same or different $Y_1$, $Y_2$, $Y_3$, $Y_4$, $Y_5$, $Y_6$, $Y_7$ or $Y_8$.

As used herein, unless specified otherwise, the term "alkyl" means a branched or unbranched, saturated or unsaturated, monovalent or multivalent hydrocarbon group. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene. In certain embodiments, the hydrocarbon group contains 1 to 20 carbons. In certain embodiments, the hydrocarbon group contains 1 to 30 carbons.

As used herein, unless specified otherwise, the term "cycloalkyl" means an alkyl which contains at least one ring and no aromatic rings. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon group contains 1 to 20 carbons. In certain embodiments, the hydrocarbon chain contains 1 to 30 carbons.

As used herein, unless specified otherwise, the term "heterocycloalkyl" means a cycloalkyl wherein at least one ring atom is a non-carbon atom. Examples of the non-carbon ring atoms include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, —$CH_2$—OH, —$OCH_3$, —O-alkyl, -alkyl-OH, -alkyl-O-alkyl-, wherein the two alkyls can be the same or different.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, -alkyl-F, -alkyl-Cl, -alkyl-Br, -alkyl-I, -alkyl(F)—, -alkyl (Cl)—, -alkyl(Br)— and -alkyl(I)—.

As used herein, unless specified otherwise, the term "alkylthio" means an alkyl, cycloalkyl or heterocycloalkyl, which contains one or more sulfur atoms. Examples of alkylthio include, but are not limited to, —$CH_2$—SH, —$SCH_3$, —S-alkyl, -alkyl-SH, -alkyl-S-alkyl-, wherein the two alkyls can be the same or different.

As used herein, unless specified otherwise, the term "alkylamino" means an alkyl, cycloalkyl or heterocycloalkyl, which contains one or more nitrogen atoms. Examples of alkylamino include, but are not limited to, —$CH_2$—NH, —$NCH_3$, —N(alkyl)-alkyl, —N-alkyl, -alkyl-$NH_2$, -alkyl-N-alkyl and -alkyl-N(alkyl)-alkyl wherein the alkyls can be the same or different.

As used herein, unless specified otherwise, the term "perfluoroalkyl" means an alkyl, cycloalkyl or heterocycloalkyl, which contains one or more perfluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur. Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl and benzothiazolyl.

In certain embodiments, the transportational unit of a HPP or HPC comprises a protonatable amine group that is capable of facilitating the transportation or crossing of the HPP through one or more biological barriers. In certain embodiments, the protonatable amine group is substantially protonated at a physiological pH. In certain embodiments, the amine group can be reversibly protonated. In certain embodiment, the transportational unit may or may not be cleaved from the functional unit after the penetration of HPP through one or more biological barriers.

In certain embodiments, the protonatable amine group is selected from the group consisting of pharmaceutically acceptable substituted or unsubstituted primary amine groups, pharmaceutically acceptable substituted or unsubstituted secondary amine groups, and pharmaceutically acceptable substituted or unsubstituted tertiary amine groups.

In certain embodiments, the protonatable amine group comprises a moiety having a structure selected from Group N, wherein Group N includes Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr:

Group N:

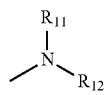

Structure Na

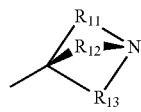

Structure Nb

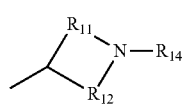

Structure Nc

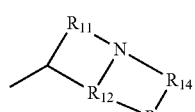

Structure Nd

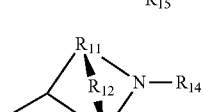

Structure N e

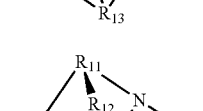

Structure Nf

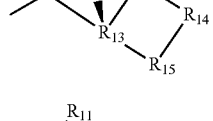

Structure N g

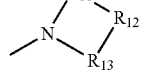

-continued

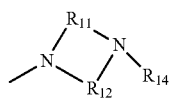

Structure Nh

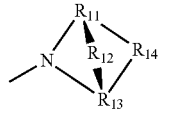

Structure Ni

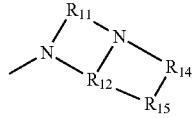

Structure Nj

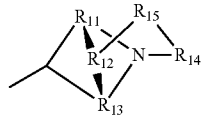

Structure Nk

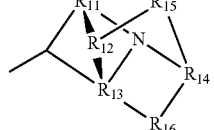

Structure N l

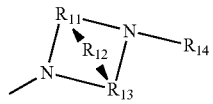

Structure Nm

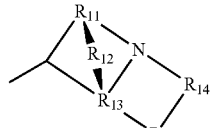

Structure N n

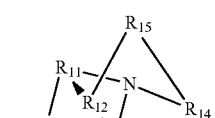

Structure No

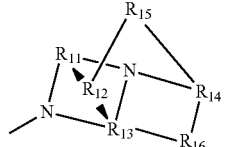

Structure N p

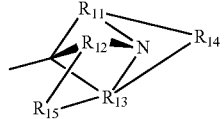

Structure N q

Structure Nr including stereoisomers and pharmaceutically acceptable salts thereof.

As used herein, unless specified otherwise, each $R_{11}$-$R_{16}$ is independently selected from the group consisting of nothing, H, $CH_2COOR_{11}$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NR_{11}$, or any other pharmaceutically acceptable groups.

In certain embodiments, the linker covalently linking the functional unit and the transportational unit of a HPP or HPC comprises a bond that is capable of being cleaved after the HPP penetrates across one or more BBs. The cleavable bond comprises, for example, a covalent bond, an ether, thioether, amide, ester, thioester, carbonate, carbamate, phosphate or oxime bond.

In certain embodiments, a HPP of a 4-aminophenol derivative has the following Structure L:

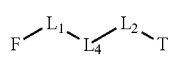

Structure L including stereoisomers and pharmaceutically acceptable salts thereof, wherein:

F comprises a moiety having a structure selected from Group F-1;

T comprises a moiety having a structure selected from Group N;

$L_1$ is selected from the group consisting of nothing, O, S, —N($L_3$)-, —N($L_3$)-$CH_2$—O, —N($L_3$)-$CH_2$—N($L_3$)-, —O—$CH_2$—O—, —O—CH($L_3$)-O, and —S—CH($L_3$)-O—;

$L_2$ is selected from the group consisting of nothing, O, S, —N($L_3$)-, —N($L_3$)-$CH_2$—O, —N($L_3$)-$CH_2$—N($L_3$)-, —O—$CH_2$—O—, —O—CH($L_3$)-O, —S—CH($L_3$)-O—, —O-$L_3$-, —N-$L_3$-, —S-$L_3$-, —N($L_3$)-$L_3$- and $L_3$;

$L_4$ is selected from the group consisting of C=O, C=S,

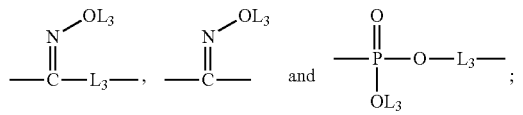

each $L_3$ is independently selected from the group consisting of nothing, H, $CH_2COOR_1$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NL_3$, or any other pharmaceutically acceptable groups.

In certain embodiments, a HPP of a 4-aminophenol derivative has the following Structure 1:

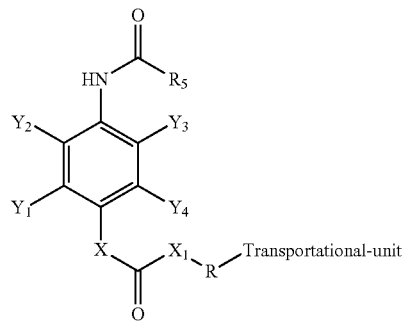

Structure 1 including stereoisomers and pharmaceutically acceptable salts thereof.

In certain embodiments, a HPP of a 4-aminophenol derivative has Structure 1, including stereoisomers and pharmaceutically acceptable salts thereof, wherein:

Transportational-unit comprises a moiety having a structure selected from Group N;

R is selected from the group consisting of 0-20 carbon atoms alkyl, 1-20 carbon atoms alkyloxyl, 1-20 carbon atoms perfluoroalkyl, 1-20 carbon atoms alkyl halide, 6-20 carbon atoms aryl, and 2-20 carbon atoms heteroaryl groups wherein any $CH_2$ may be independently replaced with O, S, $NR_5$, or other groups;

X is selected from the group consisting of O, 2-OCO—$C_6H_4$—O and 2-OCO—$C_6H_4$—O—CO—$C_6H_4$—O, wherein the benzene ring can be further substituted by one or plural of the same or different $Y_1$, $Y_2$, $Y_3$, or $Y_4$;

each $Y_1$ to $Y_4$ is independently selected from the group consisting of H, halogen, CN, $R_5$, $CH_3C\equiv C$, $CR_6\equiv C$, P(O)$OR_6$, $CF_3$, $CF_3O$, $CH_3$, $CF_3CF_2$, $CF_3CF_2O$, $CH_3CH_2$, $CH_3CH_2CH_2$, $(CH_3)_2CH$, $(CH_3)_2CHCH_2$, $CH_3CH_2CH$ $(CH_3)$, $(CH_3)_3C$, $C_4H_9$, $C_5H_{11}$, $CH_3CO_3CH_3CH_2CO$, $R_5CO$, $CH_3COO$, $R_5COO$, $R_5COOCH_2$, $R_6NHCOOCH_2$, $CH_3COS$, $CH_3O$, $R_5O$, HO, $CF_3CH_2SCH_2$, $CHCl_2$, $CH_2COOR_6$, $CH_3S$, $R_5S$, HS, $CH_3OCH_2CH_2$, $R_5OCH_2$, $R_5OCH_2CH_2$, $R_5O(C=O)$, $C_2H_5OCONH$, $CH_2NHR_8$, $CH_3OCONH$, $CH_3SO_2$, $CH_3SO$, $R_5SO_2$, $R_5SO$, $NH_2SO_2$, $C_6H_5CH_2$, $NH_2$, $NHR_5$, cyclobutyl, cyclopropyl, 4-chlorophenyl, 4-fluorophenyl, $CH_2=CH$, $CH_2=CHCH_2$, $CH_3CH=CH$, $NHR_5SO_2$, $N(R_5)_2SO_2$, $R_5OCH_2CH_2$, and $NO_2$;

$X_1$ is selected from the group consisting of nothing, O, NH, $NR_6$ and S;

each $R_5$ and $R_6$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted substituted and unsubstituted heteroaryl, substituted and unsubstituted alkoxyl, substituted and unsubstituted alkylthio, substituted and unsubstituted alkylamino, substituted and unsubstituted perfluoroalkyl, substituted and unsubstituted alkyl halide, wherein any carbon or hydrogen may be further independently replaced with O, S, N, P(O)$OR_6$, CH=CH, C≡C, $CHR_6$, $CR_5R_6$, aryl, heteroaryl, and cyclic groups.

In certain embodiments, a HPP of a 4-aminophenol derivative has the following Structure 1a:

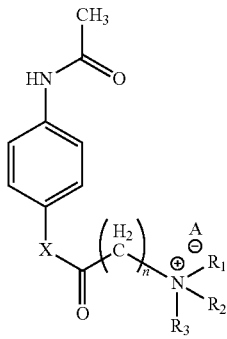

Structure 1a including stereoisomers and pharmaceutically acceptable salts thereof.

As used herein, the term "HA" is nothing or a pharmaceutically acceptable acid, e.g. hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

As used herein, "A" or "A$^-$" is nothing or a pharmaceutically acceptable anion, e.g. Cl—, Br—, F—, I—, acetylsalicylate, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate or any pharmaceutically acceptable anion.

In certain embodiments, a HPP of a 4-aminophenol derivative has Structure 1a, including stereoisomers and pharmaceutically acceptable salts thereof, wherein:

each $R_1$, $R_2$ and $R_3$ is independently selected from the group consisting of H, alkyl, alkyloxyl, alkenyl and alkynyl radicals having 1 to 12 carbon atoms and aryl radicals;

X represents O or 2-OCO—$C_6H_4$—O;

n is selected from the group of integers; and any $CH_2$ groups in $R_1$-$R_3$ may be independently replaced with O, S, or NH.

In certain embodiments, n is selected from the group of integers of 1-30. In certain embodiments, n is selected from the group of integers of 1-20. In certain embodiments, n is selected from the group of integers of 1-12.

II. Pharmaceutical Compositions Comprising HPPs

Another aspect of the invention relates to a pharmaceutical composition comprising a HPP and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a HPP from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., a HPP, of the formulation and suitable for use in contact with the tissue or organ of a biological subject without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of HPP in these formulations can vary widely, and will be selected primarily based on fluid volumes, viscosities, body weight and the like in accordance with the particular mode of administration selected and the biological subject's needs. For example, the concentration can be 0.1% to 99.5%, 10% to 70%, 5% to 20% wt.

The compositions of the invention can be administered for prophylactic, therapeutic, and/or hygienic use. Such administration can be through various delivery routes such as oral, enteral, buccal, nasal, topical, rectal, vaginal, aerosol, transmucosal, epidermal, transdermal, dermal, ophthalmic, pulmonary, subcutaneous, and/or parenteral administration. In certain embodiments, the composition of the present invention is administered orally, transdermally, topically, subcutaneously and/or parenterally The pharmaceutical compositions can be administered in a variety of unit dosage forms depending upon the method of administration. For example, unit dosage forms suitable for oral administration include powder, tablets, pills, capsules and lozenges.

Thus, a typical pharmaceutical composition for intravenous administration would be about $10^{-9}$ g to about 100 g, about $10^{-6}$ g to about 100 g, about 0.001 g to about 100 g, or about 0.01 g to about 10 g per subject per day. Dosages from about 0.01 mg, up to about 5 g, per subject per day may be used. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

In each embodiment, a pharmaceutical composition comprises a HPP of a 4-aminophenol derivative according to the present invention.

III. Applications of HPPs i) Methods for Penetrating a Biological Barrier.

Another aspect of the invention relates to a method of use of a composition of the invention in penetrating one or more BBs in a biological subject. The method comprises a step of administrating to a BB a HPP or a HPC. In certain embodiments, a HPP or HPC shows more than 100 times higher penetration rate through one or more BBs than its parent drug. In certain embodiments, a HPP or HPC shows more than 50 times higher penetration rate through one or more BBs than its parent drug.

The term "biological barrier" as used herein refers to a biological layer that separates an environment into different spatial areas or compartments, wherein the layer is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a cell layer, a biological structure, an inner surface of subjects, organisms, organs or body cavities, an external surface of subjects, organisms, organs or body cavities, or any combination or plurality thereof.

Examples of biological membrane include a lipid bilayer structure, eukaryotic cell membrane, prokaryotic cell membrane, intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies.

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of cell layers include linings of eukaryotic cells (e.g., epithelium, lamina propria and smooth muscle or muscularis mucosa (in gastrointestinal tract)), amd lining of prokaryotic cells (e.g., surface layer or S-layer which refers to a two dimensional structure monomolecular layer composed of proteins or glycoprotein). For example, a cell layer includes a biofilm (a structured community of microorganisms encapsulated within a self-developed polymeric matrix and adherent to a living or inert surface), and plant cell layer (e.g., empidermis). The cells may be normal cells or pathological cells (e.g. disease cells, cancer cells).

Examples of biological structures include structures sealed by tight or occluding junctions which provide a barrier to the entry of toxins, bacteria and viruses, e.g. the blood milk barrier and the blood brain barrier (BBB). In particular, BBB is composed of impermeable class of endothelium, which presents both a physical barrier through tight junctions adjoining neighboring endothelial cells and a transport barrier comprised of efflux transporters. The biological structure may also include a mixture of cells, proteins and sugars (e.g. blood clots).

Examples of inner surfaces of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of external surfaces of an subjects, organisms, organs or body cavities include capillaries (e.g. capillaries in the heart tissue), mucous membranes that are continuous with skin (e.g. such as at the nostrils, the lips, the ears, the genital area, and the anus) outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani), skin, cuticle (e.g., dead layers of epidermal cells or keratinocytes or superficial layer of overlapping cells covering the hair shaft of an animal, a multi-layered structure outside the epidermis of many invertebrates, plant cuticles or polymers cutin and/or cutan, external layer of the wall of a pollen grain or the external wall layer of a spore), or a combination or plurality thereof.

In addition, a biological barrier further includes a sugar layer, a protein layer or any other layer, or a combination or plurality thereof. For example, skin is a biological barrier that has a plurality of layers. The outer surface of the skin is the epidermis, which itself contains several layers: the basal cell layer, the spinous cell layer, the granular cell layer and the stratum corneum. The cells in the epidermis are called keratinocytes. The stratum corneum ("horny layer") is the top layer of the epidermis, wherein cells here are flat and scale-like ("squamous") in shape.

ii) Methods for Diagnosing a Condition in a Biological Subject.

Another aspect of the invention relates to a method of use of a composition of the invention in diagnosing a condition in a biological subject. The method comprises the following steps:

1) administrating a composition comprising a HPP or HPC to the biological subject;
2) detecting the presence, location and/or amount of the HPP in the biological subject; and
3) determining a condition in the biological subject.

In certain embodiments, a HPP (or an agent cleaved from a HPP) aggregates in the site of action where a condition occurs. In certain embodiments, the presence, the location or amount of the functional unit of a HPP is also detected. In certain embodiments, the onset, development, progress, or remission of a condition (e.g., an infection or a disease) associated is also determined based on the level of the aggregation of a HPP (or an agent cleaved from a HPP) in a site of action.

In certain embodiments, a HPP is labeled with or conjugated to a detectable agent. Alternatively, the HPP is prepared to include radioisotopes for detection.

Numerous detectable agents are available which can be generally grouped into the following categories:

(a) radioisotopes, such as $^{35}S$, $^{14}C$, $^{13}C$, $^{15}N$, $^{125}I$, $^{3}H$, and $^{131}I$ The diagnostic agent can be labeled with the radioisotope using the techniques known in the art and radioactivity can be measured using scintillation counting; in addition, the diagnostic agent can be spin labeled for electron paramagnetic resonance for carbon and nitrogen labeling;

(b) fluorescent agents such as BODIPY, BODIPY analogs, rare earth chelates (europium chelates), fluorescein and its derivatives, FITC, 5,6 carboxyfluorescein, rhodamine and its derivatives, dansyl, Lissamine, phycoerythrin, green fluorescent protein, yellow fluorescent protein, red fluorescent protein and Texas Red. Fluorescence can be quantified using a fluorometer; and (c) various enzyme-substrate agents, such luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like; examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-galactosidase) or fluorogenic substrate 4-methylumbelliferyl-β-D-galactosidase.

In certain embodiments, a detectable agent is not necessarily conjugated to the diagnostic agent but is capable of recognizing the presence of the diagnostic agent and the diagnostic agent can be detected.

In certain embodiments, a HPP or HPC of the present invention can be provided in a kit, i.e., a packaged combination of reagents in predetermined amounts with instructions for performing the diagnostic assay. When a HPP or HPC is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

iii) Methods for Screening a Substance for a Desired Character

Another aspect of the invention relates to a method of screening a HPP for a desired character.

In certain embodiments, the method comprises:
1) covalently linking a test functional unit to a transportational unit through a linker to form a test composition (or covalently linking a functional unit to a test transportational unit through a linker, or covalently linking a functional unit to a transportational unit through a test linker)
2) administrating a test composition to a biological subject; and
3) determining whether the test composition has a desired character.

In one embodiment, the desired character may include, for example, 1) the ability of a test functional unit to form a high penetration composition or convert back to a parent drug, 2) the penetration ability and/or rate of a test composition, 3) the efficiency and/or efficacy of a test composition, 4) the transportational ability of a test transportational unit, 5) the cleavability of a test linker.

iv) Methods for Treating a Condition in a Biological Subject

Another aspect of the invention relates to a method of use of a HPC or HPP in treating a condition in a biological subject. The method comprises administrating the HPC or HPP to the biological subject. Examples of the conditions the method can treat include conditions that can be treated by a parent drug of a HPP.

The term "treating" as used herein means curing, alleviating, inhibiting, or preventing. The term "treat" as used herein means cure, alleviate, inhibit, or prevent. The term "treatment" as used herein means cure, alleviation, inhibition or prevention.

The term "biological system," "biological subject" or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism. In at least some form, all organisms are capable of response to stimuli, reproduction, growth and development, and maintenance of homeostasis as a stable whole The term "animal" as used herein means an eukaryotic organism characterized by voluntary movement. Examples of animal include, without limitation, vertebrata (e.g. human, mammals, birds, reptiles, amphibians, fishes, marsipobranchiata and leptocardia), tunicata (e.g. thaliacea, appendicularia, sorberacea and ascidioidea), articulata (e.g. insecta, myriapoda, malacapoda, arachnida, pycnogonida, merostomata, crustacea and annelida), gehyrea (anarthropoda) and helminthes (e.g. rotifera).

The term "plant" as used herein means organisms belonging to the kindom Plantae. Examples of plant include, without limitation, seed plants, bryophytes, ferns and the fern allies. Examples of seed plants include, without limitation, cycads, ginkgo, conifers, gnetophytes and angiosperms. Examples of bryophytes include, without limitation, liverworts, hornworts and mosses. Examples of ferns include, without limitation, ophioglossales (e.g. adderstongues, moonworts and grape-ferns), marattiaceae and leptosporangiate ferns. Examples of fern allies include, without limitation, lycopsida (e.g. clubmosses, spikemosses and quillworts), psilotaceae (e.g. lycopodiophyta and whisk ferns) and equisetaceae (e.g. horsetails).

The term "fungus" as used herein means a eukaryotic organism that is a member of the kingdom Fungi. Examples of fungus include, without limitation, chytrids, blastocladiomycota, neocallimastigomycota, zygomycota, glomeromycota, ascomycota and basidiomycota.

The term "micro-organism" as used herein means an organism that is microscopic (e.g. with length scale of micrometer). Examples of micro-organism include, without limitation, bacteria, fungi, archaea, protists, microscopic plants (e.g. green algae) and microscopic animals (e.g. plankton, planarian and amoeba).

Another aspect of the invention relates to a method of use of a HPP composition of a 4-aminophenol derivative in treating a condition in a biological subject by administrating a HPP of a 4-aminophenol derivative to the biological subject.

Some examples of conditions treatable by the method of using a HPP or HPC of 4-aminophenol derivatives include:
1) autoimmune disease, e.g. discoid lupus erythematosus, systemic lupus erythematosus (SLE), autoimmune hepatitis, cleroderma, Sjogren's syndrome, rheumatoid arthritis, polymyositis, scleroderma, Hashimoto's thyroiditis, juvenile diabetes mellitus, Addison disease, vitiligo, pernicious anemia, glomerulonephritis, pulmonary fibrosis, multiple sclerosis (MS) and Crohn's disease;
2) pain;
3) injuries;
4) fever; and
5) neurodegenerative disease, e.g. Alzheimer's diseases and Parkinson's disease.

In certain embodiments, the method of treating a condition amelioratable or treatable with a 4-aminophenol derivative or related compounds thereof, comprises administering a HPP of a 4-aminophenol derivative or related compounds thereof to a subject. Examples of the condition include, for instance, rheumatoid arthritis, osteoarthritis, fever, pain, injuries Alzheimer's diseases, Parkinson's diseases and other neurodegenerative diseases.

In certain embodiments, a HPP of a 4-aminophenol derivative shows analgesic activities. In certain embodiments, a HPP of a 4-aminophenol derivative shows antipyretic activities.

IV. Administration of HPP or HPC

A HPP or HPP composition of the invention (e.g. HPP of 4-aminophenol derivative) can be administered to a biological subject by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

A HPP or HPP composition can be given to a subject in the form of formulations or preparations suitable for each administration route. The formulations useful in the methods of the present invention include one or more HPPs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a HPP which can be combined with a carrier material to produce a pharmaceutically effective dose will generally be that amount of a HPP which produces a therapeutic effect. Generally, out of one hundred percent, this amount will range from about 1 percent to about ninety-nine percent of the HPP, preferably from about 20 percent to about 70 percent.

Methods of preparing these formulations or compositions include the step of bringing into association a HPP with one or more pharmaceutically acceptable carriers and, optionally, one or more accessory ingredients. In general, the formulations are prepared by uniformly and intimately bringing into association a HPP or HPC with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a HPP as an active ingredient. A compound may also be administered as a bolus, electuary, or paste.

In solid dosage forms for oral administration (e. g., capsules, tablets, pills, dragees, powders, granules and the like), a HPP or HPC is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a HPP or HPC therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPP(s) or HPC(s) only, or preferentially, in a certain portion of the gastrointestinal tract, optionally, in a delayed manner. Examples of embedding compositions which can be used include polymeric substances and waxes. A HPP or HPC can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to a HPP or HPC, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to a HPP or hPC, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPPs or HPC(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of a HPP composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the HPP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPP composition, excipients such as lactose, talc, silicic acid, aluminum hydroxide, calcium silicates and polyimide powder, or mixtures of these substances. Sprays can additionally contain customary propellants, such as chlorofluorohydrocarbons and volatile unsubstituted hydrocarbons, such as butane and propane.

A HPP composition can be alternatively administered by aerosol. This is accomplished by preparing an aqueous aerosol, liposomal preparation or solid particles containing the HPPs. A nonaqueous (e. g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver HPP compositions to an infection site. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Formulations suitable for parenteral administration comprise a HPP or HPC in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e. g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of a HPP or HPC or in biodegradable polymers such as polylactide-polyglycolide. Depending on the ratio of the HPP or HPC to polymer, and the nature of the particular polymer employed, the rate of drug release can be controlled. Examples of other biodegradable polymers include poly (orthoesters) and poly (anhydrides). Depot injectable formulations are also prepared by entrapping the HPP in liposomes or microemulsions which are compatible with body tissue.

In an embodiment of the invention, a HPP composition is delivered to a disease or infection site in a therapeutically effective dose. As is known in the art of pharmacology, the precise amount of the pharmaceutically effective dose of a HPP that will yield the most effective results in terms of efficacy of treatment in a given patient will depend upon, for example, the activity, the particular nature, pharmacokinetics, pharmacodynamics, and bioavailability of a particular HPP, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of a disease caused by pathogenic target microbial organisms, to name a few. However, the above guidelines can be used as the basis for fine-tuning the treatment, e. g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins PA, USA) (2000).

In certain embodiments, a composition of a HPP of a 4-aminophenol derivative is administrated to a biological subject through any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration.

V. Advantages

In certain embodiments, since a HPP of the present invention is capable of crossing one or more biological barriers, the HPP can be administered locally (e.g., typically or transdermally) to reach a location where a condition occurs without the necessity of a systematic administration (e.g., oral or parenteral administration). The local administration and penetration of a HPP or HPC allow the HPP or HPC to reach the same level of local concentration of an agent or drug with much less amount or dosage of HPP in comparison to a systematic administration of a parent agent or drug; alternatively, a higher level of local concentration which may not be afforded in the systematic administration, or if possible, requires significantly higher dosage of an agent in the systematic administration. The high local concentration of a HPP or HPC or its parent agent if being cleaved enables the treatment of a condition more effectively or much faster than a systematically delivered parent agent and the treatment of new conditions that may not be possible or observed before. The local administration of a HPP or HPC may allow a biological subject to reduce potential sufferings from a systemic administration, e.g., adverse reactions associated with the systematic exposure to the agent, gastrointestinal/renal effects. Additionally, the local administration may allow a HPP or HPC to cross a plurality of biological barriers and reach systematically through, for example, general circulation and thus avoid the needs for systematic administration (e.g., injection) and obviate the pain associated with the parenteral injection.

In certain embodiments, a HPP or HPC according to the present invention can be administered systematically (e.g., orally or parenterally). The HPP or the active agent (e.g., drug or metabolite) of the HPP may enter the general circulation with a faster rate than the parent agent and gain faster access to the action site of a condition. Additionally, the HPP can cross a biological barrier (e.g., BBB) which has not been penetrated if a parent agent is administered and thus offer novel treatment of conditions that may not be possible or observed before.

VI. Examples

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1. Preparation of a HPP from a Parent Drug

In certain embodiments, a parent compound having the following Structure P:

Structure P reacts with a compound having the following structure Q:

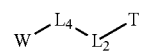

Strcuture Q to obtain a HPP of Structure L:

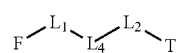

Structure L including stereoisomers and pharmaceutically acceptable salts thereof, wherein:

F, $L_{1-4}$ and T are defined as supra; and

W is selected from the group consisting of OH, halogen, alkoxycarbonyl and substituted aryloxycarbonyloxy. (Scheme 1)

Scheme 1. Preparation of a HPP from a parent compound.

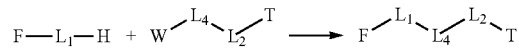

Preparation of N-Acetyl-p-Aminophenyl Dimethylaminobutyrate.HCl 15.1 g (0.1 mol) of acetaminophen was dissolved in 200 ml of acetone and 200 ml of 10% $NaHCO_3$. 18.6 g (0.1 mol) of dimethylaminobutyryl chloride hydrochloride was added into the mixture was stirred for 3 hours at RT. The solvents were evaporated off. 500 ml of ethyl acetate was added into the reaction mixture and the mixture was washed with 5% $NaHCO_3$ (1×200 ml) and water (3×100 ml). The organic solution was dried over anhydrous sodium sulfate. Sodium sulfate was removed by filtration. HCl gas was bubbled into the solution. The solid product was collected by filtration. After drying, it yielded 26 g of the HPP product (86.4%). Elementary analysis: $C_{14}H_{21}ClN_2O_3$; MW: 300.78. Calculated % C: 55.90; H: 7.04; Cl: 11.79; N: 9.31; O: 15.96; Found % C: 55.96; H: 7.06; Cl: 11.76; N: 9.29; O: 15.93. $^1$H-NMR (400 MHz, $D_2O$): δ: 1.98 (s, 3H), 2.01 (m, 2H), 2.21 (m, 2H), 2.90 (s, 6H), 3.24 (m, 2H), 7.05 (m, 2H), 7.60 (m, 2H), 7.80 (b, 1H).

Preparation of N-Acetyl-p-Aminophenyl Diethylaminobutyrate.HCl 15.1 g (0.1 mol) of acetaminophen and 16 g (0.1 mol) of diethylaminobutyric acid were dissolved in 300 ml of dichloromethylene. The mixture was cooled to 0° C. with ice bath. 20.6 g (0.1 mol) of N, N"-Dicyclohexylcarbodiimide was added into the reaction mixture. The mixture was stirred for 1 hour at 0° C. and 2 hours at RT. The solid is removed by filtration. The dichloromethylene solution was washed with 5% $NaHCO_3$ (2×100 ml) and water (3×100 ml). The organic solution was dried over anhydrous sodium sulfate. Sodium sulfate was removed by filtration. 6 g of acetic acid was added into the reaction mixture with stirring. The solid product was collected by filtration. After drying, it yielded 27 g of the HPP product (82.1%). Elementary analysis: $C_{16}H_{25}ClN_2O_3$; MW: 328.83. Calculated % C: 58.44; H: 7.66; Cl: 10.78; N: 8.52; O: 14.60; Found % C: 58.40; H: 7.68; Cl: 10.76; N: 8.55; O: 14.61. $^1$H-NMR (400 MHz, $D_2O$): δ: 1.50 (t, 6H), 2.00 (m, 2H), 2.02 (s, 3H), 2.21 (m, 2H), 3.24 (m, 2H), 3.27 (m, 4H), 7.05 (m, 2H), 7.60 (m, 2H), 7.80 (b, 1H).

Preparation of 4-acetamidophenyl 2((4-(dimethylamino)butanoyl)oxy)benzoate.HCl 27.1 g (0.1 mol) of acetaminosalol was dissolved in 200 ml of acetone and 200 ml of 10% $NaHCO_3$. 18.6 g (0.1 mol) of dimethylaminobutyryl chloride hydrochloride was added into the mixture was stirred for 3 hours at RT. The solvents were evaporated off. 500 ml of ethyl acetate was added into the reaction mixture and the mixture was washed with 5% $NaHCO_3$ (1×200 ml) and water (3×100 ml). The organic solution was dried over anhydrous sodium sulfate. Sodium sulfate was removed by filtration. HCl gas was bubbled into the solution. The solid product was collected by filtration. After drying, it yielded 36 g of the desired product (85.5%). Elementary analysis: $C_{21}H_{25}ClN_2O_5$; MW: 420.89. Calculated % C: 59.93; H: 5.99; Cl: 8.42; N: 6.66; O: 19.01; Found % C: 59.96; H: 6.02; Cl: 8.40; N: 6.64; O: 18.98. $^1$H-NMR (400 MHz, $D_2O$): δ: 1.99 (s, 3H), 2.01 (m, 2H), 2.21 (m, 2H), 2.90 (s, 6H), 3.24 (m, 2H), 7.13 (m, 2H), 7.22 (m, 2H), 7.47 (m, 1H), 7.60 (m, 2H), 7.80 (b, 1H), 8.10 (m, 1H).

Preparation of 4-acetamidophenyl 2((4-(dimethylamino)butanoyl)oxy)benzoate.HCl 27.1 g (0.1 mol) of acetaminosalol and 16 g (0.1 mol) of diethylaminobutyric acid were dissolved in 300 ml of dichloromethylene. The mixture was cooled to 0° C. with ice bath. 20.6 g (0.1 mol) of N, N'-Dicyclohexylcarbodiimide was added into the reaction mixture. The mixture was stirred for 1 hour at 0° C. and 2 hours at RT. The solid was removed by filtration. The dichloromethylene solution was washed with 5% $NaHCO_3$ (2×100 ml) and water (3×100 ml). The organic solution was dried over anhydrous sodium sulfate. Sodium sulfate was removed by filtration. 6 g of acetic acid was added into the reaction mixture with stirring. The solid product was collected by filtration. After drying, it yielded 39 g of the HPP product (86.9%). Elementary analysis: $C_{23}H_{29}ClN_2O_5$; MW: 448.94. Calculated % C: 61.53; H: 6.51; Cl: 7.90; N: 6.24; O: 17.82; Found % C: 61.50; H: 6.56; Cl: 7.85; N: 6.22; O: 17.87. $^1$H-NMR (400 MHz, $D_2O$): δ: 1.50 (t, 6H), 2.00 (m, 2H), 2.02 (s, 3H), 2.21 (m, 2H), 3.24 (m, 2H), 3.27 (m, 4H), 7.11 (m, 2H), 7.21 (m, 2H), 7.47 (m, 1H), 7.65 (m, 2H), 7.80 (b, 1H), 8.10 (m, 1H).

Example 2. HPPs of 4-Aminophenol Derivatives Showed Higher Aqueous Solubility Comparing to their Parent Drugs HPPs of 4-aminophenol derivatives had higher aqueous solubility comparing to their parent drugs (Table 1).

TABLE 1

Solubility of HPPs and parent drugs

| HPP | (g/L) | Parent Drug | (g/L) |
|---|---|---|---|
| N-Acetyl-p-aminophenyl dimethylaminobutyrate•HCl | >400 | N-Acetyl-p-aminophenol (acetaminophen) | <0.2 |
| 4-acetamidophenyl 2((4-(dimethylamino)butanoyl)oxy)benzoate•HCl | >400 | 4-acetamidophenyl salicylate (acetaminosalol) | <0.1 |

Example 3. HPPs of 4-Aminophenol Derivatives Showed Higher In Vitro Penetration Rates Across Human Skin Comparing to their Parent Drugs The penetration rates of HPPs of 4-aminophenol derivatives and their parent drugs through human skin were measured in vitro by modified Franz cells. The Franz cells had two chambers, the top sample chamber and the bottom receptor chamber. The human skin tissue (360-400 μm thick) that separated the top and the receptor chambers was isolated from the anterior or posterior thigh areas.

The compound tested (2 mL, 20% in 0.2 M phosphate buffer, pH. 7.4) were added to the sample chamber of a Franz cell. The receptor chamber contained 10 ml of 2% bovine serum albumin in saline which was stirred at 600 rpm. The amount of the tested compound penetrating the skin was determined by high-performance liquid chromatography (HPLC) method. The results were shown in FIG. 1. The apparent flux values of the tested compounds were calculated from the slopes in FIG. 1 and summarized in Table 2.

The lowest detectable apparent flux values in this method was 1 μg/cm$^2$/h, the parent drugs tested (e.g. acetaminophen and acetaminosalol) had detectable apparent flux value, and the corresponding HPPs had higher apparent flux value.

TABLE 2

In vitro Penetration rate of prodrug compounds and parent drugs

| Prodrug compounds | μg/cm$^2$/h | Parent compounds | μg/cm$^2$/h |
|---|---|---|---|
| N-acetyl-p-aminophenyl dimethylaminobutyrate•HCl | 1500 | acetaminophen | 10 |
| 4-acetamidophenyl 2((4-(dimethylamino)butanoyl)oxy)benzoate•HCl | 1800 | acetaminosalol | 10 |

Example 4. In Vivo Transportation of HPPs

A. Transportation of HPPs into Plasma

Figure 2:
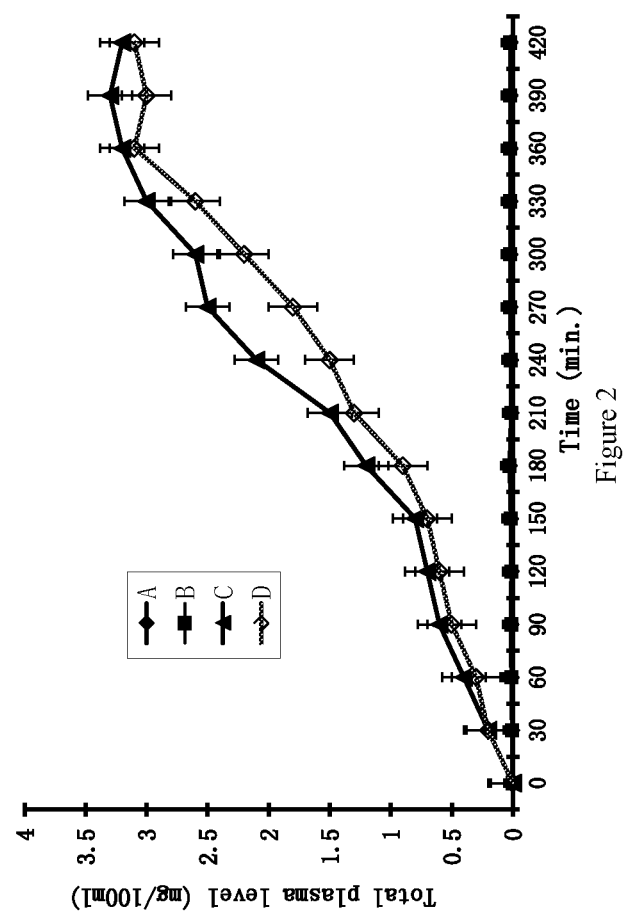
FIG. 2: Total plasma levels of acetaminophen and acetaminosalol after topical application of 1 mL of N-acetyl-p-aminophenyl dimethylaminobutyrate.HCl (A, 20% solution), 4-acetamidophenyl salicylyl dimethylaminobutyrate.HCl (B, 20% solution), acetaminophen (C, 20% suspension) and acetaminosalol (D, 20% suspension) in 70% ethanol to the backs of hairless mice (n=7) respectively.

Test compounds (20% solution or suspension of HPPs or parent drugs in 1 ml of 70% ethanol) were administered transdermally to 10 cm$^2$ skin on the backs of hairless mice. The plasma levels of the parent compounds were determined by HPLC. The results showed that HPP were converted to their parent drugs within a short period of time after administration. The peak levels of the active compounds in plasma were reached in around 50 minutes after the transdermal administration of the HPPs (FIG. 2), which was shorter than the time required to reach the plasma peak levels of the parent drugs when the parent drugs were taken orally. The Peak plasma levels of the prodrug compounds and the parent compounds were summarized in Table 3.

TABLE 3

Plasma concentration of the parent compounds after administration of prodrug compounds and parent compounds.

| Prodrug compound | t min | mg/L | Parent compound | t (h) | mg/L |
|---|---|---|---|---|---|
| N-acetyl-p-aminophenyl dimethylaminobutyrate•HCl | ~50 | 30.0 | acetaminophen | ~5 | 0.1 |
| 4-acetamidophenyl 2((4-(dimethylamino)butanoyl)oxy) benzoate•HCl | ~50 | 30.0 | acetaminosalol | ~5 | 0.1 |

B) In Vivo Transportation of HPPs.

N-Acetyl-p-aminophenyl dimethylaminobutyrate.HCl (20% in 1 mL of 50% ethanol) was applied to about 10 cm$^2$ skin on the backs of rats (~200 g). After 6 hours, the rats were terminated, and methanol (5 mL) was added to 1 g of tissue on the back of rat (under the skin), 1 ml of blood, 1 g of liver, 1 g of kidney, and 1 g of brain respectively (the tissue, liver, kidney or brain was washed with pH 7.2 buffer for three times) and the mixtures were homogenized. The samples were then centrifuged for 5 min and analyzed using HPLC. The amounts of N-acetyl-p-aminophenyl dimethylaminobutyrate and acetaminophen in each organ and tissue were summarized in Table 4.

TABLE 4

In vivo transportation of N-Acetyl-p-aminophenyl dimethylaminobutyrate•HCl

| Compound detected in vivo | Under-skin tissue (μg/g) | Blood (μg/g) | Liver (μg/g) | Kidney (μg/g) | Brain (μg/g) |
|---|---|---|---|---|---|
| acetaminophen | 60 ± 10 | 30 ± 8 | 20 ± 10 | 20 ± 10 | 10 ± 8 |
| N-acetyl-p-aminophenyl dimethylaminobutyrate | 15 ± 8 | 10 ± 4 | 7 ± 4 | 6 ± 4 | 3 ± 3 |

Example 5. Acute Toxicity of HPP and Parent Drug

The acute toxicity of prodrug compounds and parent compounds were measured by $LD_{50}$ of rat. As used herein, the term "$LD_{50}$" is the dose that kills 50% of the animal tested. The results (Table 5) showed that the prodrug compounds were less toxic than the corresponding parent compounds.

TABLE 5

The acute toxicity of HPP and their parent drugs in mice ($LD_{50}$).

| HPP | $LD_{50}$ (g/kg) | Parent Drug | $LD_{50}$ (g/kg) |
|---|---|---|---|
| N-acetyl-p-aminophenyl dimethylaminobutyrate•HCl | 0.65 | acetaminophen | 0.34 |
| 4-acetamidophenyl 2((4-(dimethylamino)butanoyl)oxy) benzoate•HCl | 0.67 | acetaminosalol | 0.55 |

Example 6. Analgesic Activities of HPPs and their Parent Drugs

The analgesic activities of prodrug compounds and parent compounds were determined using the D'Amour-Smith Method (J. Pharmacol. Exp. Ther., 72, 74(1941)).

Figure 3:
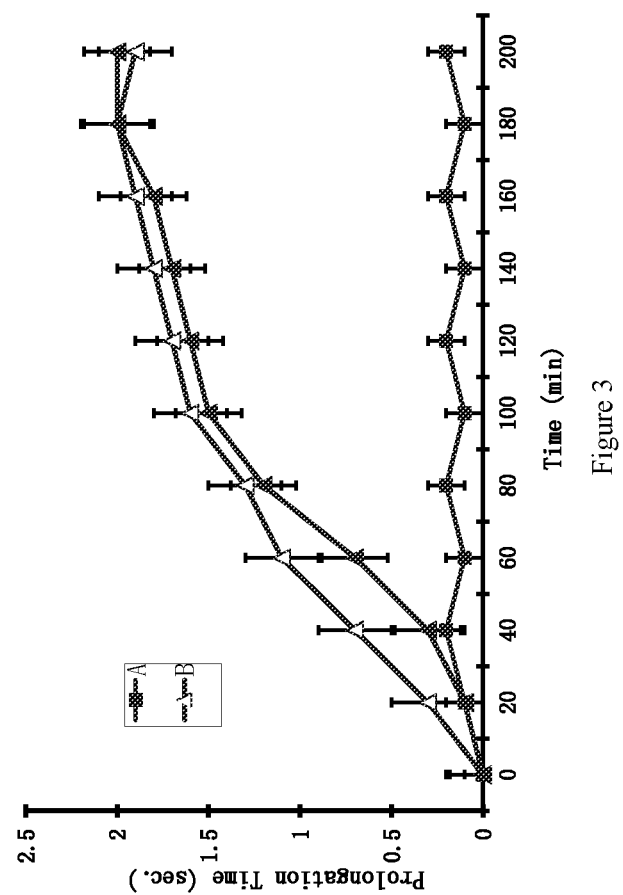
FIG. 3. The prolongation time of the pain threshold of mice (tails) after 50 mg/kg of N-acetyl-p-aminophenyl dimethylaminobutyrate.HCl (B) and 4-acetamidophenyl salicy-lyl dimethylaminobutyrate.HCl (C) were administered transdermally respectively. Group A is the control group.

After the tested compounds were administered transdermally (50 mg/kg) to a group of mice (six mice every group), the tails of the mice were exposed to heat and the prolongation time of pain threshold was determined. The results showed that the prodrug compounds had analgesic activities. (FIG. 3)

Acetic acid solution was administered intraperitoneally to a group of mice (6 mice every group) 120 minutes after a test compound was administered to the mice at the dosage specified in the tables below. The prodrug compounds were administered either transdermally or orally. N-acetyl-p-aminophenyl dimethylaminobutyrate.HCl (100 mg/kg, B) and 4-acetamidophenyl 2((4-(dimethylamino)butanoyl)oxy) benzoate.HCl, (100 mg/kg, C) were administered transdermally. The number of writhings that occurred when mice were administered the acetic acid solution were counted, and the rate of inhibition based on the control group which was not pretreated with any test compounds was calculated. The results showed that the prodrug compounds have analgesic activities. Group A was the control group. The results are shown in Table 6.

TABLE 6

The rate of writhings inhibition by prodrugs of acetaminophen and acetaminosalol

| Group | Dose (mg/kg) | No. of Writhings | % |
|---|---|---|---|
| A | 0 | 35.0 | — |
| B | 100 | 15.6 | 55 |
| C | 100 | 15.7 | 55 |

Example 7. Antipyretic Activities of Prodrug Compounds Comparing to their Parent Compounds Rats received a sterilized *E. coli* suspension as a pyrogen. The control group was group A. 2 hours later, N-acetyl-p-aminophenyl dimethylaminobutyrate.HCl (100 mg/kg, B) and 4-acetamidophenyl 2((4-(dimethylamino)butanoyl)oxy) benzoate.HCl, (100 mg/kg, C) were administered transdermally respectively. The body temperature of rats was taken at 90 min. intervals before and after the administration of the test compounds. The results are shown in Table 7.

TABLE 7

Antipyretic Activity of prodrugs of acetaminophen and acetaminosalol

| Compound | t = 0 min. | t = 90 min. | t = 180 min. | t = 270 min. |
|---|---|---|---|---|
| A (Control group) | 37.34 ± 0.05 | 37.36 ± 0.07 | 37.37 ± 0.05 | 37.44 ± 0.08 |
| B (100 mg/kg) | 37.32 ± 0.06 | 36.61 ± 0.05 | 36.50 ± 0.08 | 36.50 ± 0.07 |
| C (100 mg/kg) | 37.27 ± 0.06 | 36.63 ± 0.05 | 36.52 ± 0.08 | 36.50 ± 0.07 |

The invention claimed is:
1. A compound having the structure:

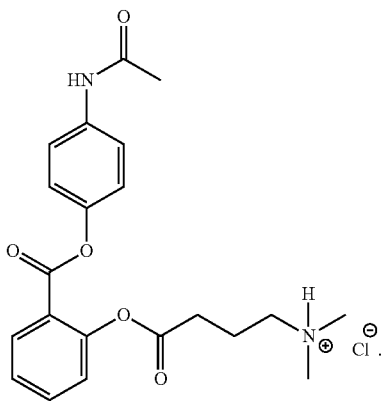 [SMILES: CC(=O)Nc1ccc(OC(=O)c2ccccc2OC(=O)CCC[NH+](C)C)cc1 ; [Cl-]]

2. A composition comprising a compound according to Structure 1a:

Structure 1a

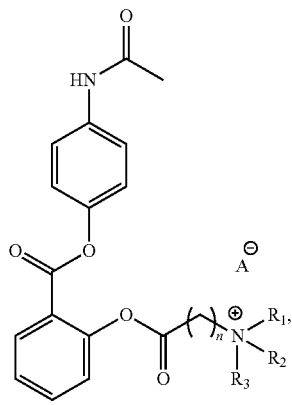

wherein $R_1$ and $R_2$ are each ethyl;
$R_3$ is H;
$A^-$ is $Cl^-$; and
n is 1, 2, 3, 4, 5, 6, 7, 8, 9, or 10.

3. The composition according to claim 2, further comprising a pharmaceutically acceptable carrier.

4. The composition according to claim 3, wherein the pharmaceutically acceptable carrier is polar.

5. The composition according to claim 3, wherein the pharmaceutically acceptable carrier is selected from the group consisiting of alcohol, acetone, ester, buffer, water, isotonic saline and Ringers solution.

6. The composition according to claim 2, further comprising a pharmaceutically acceptable auxiliary agent selected from the group consisting of pH adjusting agents, buffering agents, and toxicity adjusting agents.

7. The composition according to claim 2, wherein the concentration of the compound is from 5 weight percent to 20 weight percent.

8. The composition according to claim 2, wherein the composition is formulated for transdermal administration.

9. The composition according to claim 8, wherein the composition is formulated as a transdermal patch.

10. The composition according to claim 2, wherein the composition is formulated as a solution, a spray, a lotion, an ointment, an emulsion or a gel.

11. The composition according to claim 10, wherein the composition is formulated as a spray.

12. The composition according to claim 11, wherein the spray is administered orally or nasally.

* * * * *